(12) United States Patent
Yokoyama et al.

(10) Patent No.: US 8,999,124 B2
(45) Date of Patent: Apr. 7, 2015

(54) DETECTION DEVICE

(75) Inventors: Takao Yokoyama, Tokyo (JP); Reiko Machida, Takasaki (JP); Yayoi Irie, Takasaki (JP); Yoshihiko Umegae, Takasaki (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 163 days.

(21) Appl. No.: 13/582,257

(22) PCT Filed: Mar. 2, 2011

(86) PCT No.: PCT/JP2011/054734
§ 371 (c)(1),
(2), (4) Date: Aug. 31, 2012

(87) PCT Pub. No.: WO2011/108576
PCT Pub. Date: Sep. 9, 2011

(65) Prior Publication Data
US 2012/0325658 A1    Dec. 27, 2012

(30) Foreign Application Priority Data
Mar. 3, 2010    (JP) .................................. 2010-046813

(51) Int. Cl.
*G01N 27/26*    (2006.01)
*G01N 27/327*    (2006.01)
(Continued)

(52) U.S. Cl.
CPC ...... *G01N 27/3272* (2013.01); *B01L 3/502715* (2013.01); *B01L 3/502738* (2013.01);
(Continued)

(58) Field of Classification Search
CPC ... G01N 27/327; B01L 3/502; B01L 2400/04; B01L 2400/065; B01L 2200/027; B01L 2300/0645

USPC ............ 204/403.01–403.15; 422/82.01, 68.1; 435/287.1
See application file for complete search history.

(56) References Cited

U.S. PATENT DOCUMENTS 5,541,057 A * 7/1996 Bogart et al. ...................... 435/5
2004/0040868 A1 * 3/2004 DeNuzzio et al. ............ 205/792
(Continued)

FOREIGN PATENT DOCUMENTS

| JP | 11-344461 A | 12/1999 |
| JP | 2000-508423 A | 7/2000 |

(Continued)

OTHER PUBLICATIONS

U.S. Appl. No. 61/162,922, filed Mar. 24, 2009.*
(Continued)

*Primary Examiner* — Jennifer Dieterle
(74) *Attorney, Agent, or Firm* — Leason Ellis LLP.

(57) ABSTRACT

A detection device that is used to detect a sample includes: a base component having on its surface a sample supply position to which the sample is supplied; an electrode system formed at a distance from the sample supply position on the surface of the base component; a sliding component having a slide body that performs a sliding movement over the surface of the base component, a sample receptacle portion provided in a portion of the slide body; and a supporting portion that is fixed to the base component and supports the sliding component such that it can perform the sliding movement relative to the base component. The base and the sliding components can perform the sliding movement within a range that includes an overlap position, where the sample receptacle portion overlaps with the electrode system, and the sample supply position.

19 Claims, 18 Drawing Sheets

(51) Int. Cl.
*B01L 3/00* (2006.01)
*G01N 21/78* (2006.01)
*G01N 35/10* (2006.01)

(52) U.S. Cl.
CPC .......... *G01N21/78* (2013.01); *B01L 2200/027* (2013.01); *B01L 2300/0645* (2013.01); *B01L 2300/0825* (2013.01); *B01L 2400/0406* (2013.01); *B01L 2400/0475* (2013.01); *B01L 2400/065* (2013.01); *G01N 35/1016* (2013.01)

(56) References Cited

U.S. PATENT DOCUMENTS

| | | | |
|---|---|---|---|
| 2004/0072357 A1* | 4/2004 | Stiene et al. | 436/69 |
| 2004/0119070 A1 | 6/2004 | Roach et al. | |
| 2008/0058039 A1* | 3/2008 | Lee et al. | 455/575.4 |
| 2009/0105095 A1* | 4/2009 | Deutsch | 506/39 |
| 2009/0178924 A1* | 7/2009 | Ala-Kleme et al. | 204/403.06 |
| 2011/0031118 A1* | 2/2011 | Machida et al. | 204/403.14 |
| 2012/0028342 A1* | 2/2012 | Ismagilov et al. | 435/283.1 |
| 2012/0264232 A1* | 10/2012 | Kramer et al. | 436/501 |

FOREIGN PATENT DOCUMENTS

| | | |
|---|---|---|
| JP | 2003-043052 A | 2/2003 |
| JP | 2005-083505 A | 3/2005 |
| JP | 2005-083510 A | 3/2005 |
| JP | 2006-242773 A | 9/2006 |
| JP | 2008-020287 A | 1/2008 |
| JP | 2008-096238 A | 4/2008 |
| JP | 2009-171988 A | 8/2009 |
| JP | 2011-163882 A | 8/2011 |
| WO | WO-02/86483 A | 10/2002 |
| WO | WO-2006/018044 A | 2/2006 |
| WO | WO-2008/072702 A1 | 6/2008 |
| WO | WO 2009060849 * | 5/2009 |
| WO | WO 2010111265 * | 9/2010 |

OTHER PUBLICATIONS

International Search Report mailed May 24, 2011 for the corresponding PCT Application No. PCT/JP2011/054734.

Office Action mailed Feb. 10, 2015 for the related Japanese Application No. 2012-503207.

* cited by examiner

DETECTION DEVICE

CROSS-REFERENCE TO RELATED PATENT APPLICATIONS

This application is a U.S. National Phase Application under 35 U.S.C. §371 of International Patent Application No. PCT/JP2011/054734, filed Mar. 2, 2011, and claims the benefit of Japanese Patent Application No. 2010-046813, filed Mar. 3, 2010, all of which are incorporated by reference herein. The International Application was published in Japanese on Sep. 9, 2011 as International Publication No. WO/2011/108576 under PCT Article 21(2).

FIELD OF THE INVENTION

The present invention relates to a detection device that is used to detect substances in a test sample.

BACKGROUND ART OF THE INVENTION

In recent years, 1,5-anhydroglucitol (hereinafter, referred to as '1,5-AG') has garnered attention as a marker which can be used to ascertain the glycemic control state of diabetes sufferers. 1,5-AG has the advantages that it is largely unaffected by food intake, and that it reflects the glycemic control state for a comparatively short period such as the previous week or so.

For example, using human whole blood as a sample, in order to detect 1,5-AG, multi-stage processing is performed in which, firstly, any substances that might obstruct the detection of the 1,5-AG are removed from the whole blood sample, and then the detection of the 1,5-AG is performed.

As the detection device that is used to perform this multistage processing on a sample, for example, a biosensor that performs a two-stage reaction in order to detect the concentration of glycoprotein in blood is disclosed in Patent document 1. This biosensor has a suction cavity that suctions the sample by using a capillary phenomenon, an analysis cavity that performs an enzymic reaction on the sample, and a flow passage that connects the suction cavity and the analysis cavity together. A preprocessing reagent is immobilized in the suction cavity. In this biosensor, once the sample has been suctioned into the suction cavity by the capillary phenomenon, preprocessing is then performed in the suction cavity. Once the sample has completed the preprocessing, it is moved from the suction cavity to the analysis cavity by centrifugal force, and an enzymic reaction is then generated.

DOCUMENTS OF THE PRIOR ART

Patent Documents

[Patent document 1] Japanese Unexamined Patent Application, First Publication No. 2008-20287

Problems to be Solved by the Invention

However, in the biosensor described in Patent document 1, in order to move the sample from the suction cavity to the analysis cavity by means of centrifugal force, a rotating platform on which the biosensor can be mounted and that is able to rotate the biosensor at high speed is required. As a consequence, the device structure of the inspection instruments that perform inspections using the biosensor has had to be very complex. Moreover, if the biosensor described in Patent document 1 is rotated at high speed, there is a possibility that the sample will be spattered around the rotating platform, and it has been necessary to pay careful attention to ensuring that the area surrounding the rotating platform remains hygienic.

The present invention is conceived in view of the above-described circumstances, and it is an object thereof to provide a detection device that has a simple structure and is able to perform multistage processing safely.

SUMMARY OF THE INVENTION

Means for Solving the Problem

In order to solve the above-described problems, this invention proposes the following means.

The detection device of the present invention is a detection device that is used to detect a sample, and that includes: a base component having on its surface a sample supply position to which the sample is supplied; a detecting section that is formed at a distance from the sample supply position on the surface of the base component; a sliding component having a slide body that performs a sliding movement over the surface of the base component, and also having a sample receptacle portion that is provided in a portion of the slide body and is able to contain the sample: and a supporting portion that is fixed to the base component and supports the sliding component such that it is able to perform the sliding movement relative to the base component, wherein the base component and the sliding component are able to perform the sliding movement within a range that includes an overlap position, where the sample receptacle portion overlaps with the detecting section, and the sample supply position.

According to the detection device of the present invention, as a result of the sliding component performing a sliding movement, a sample that was contained within the sample receptacle portion at the sample supply position is moved from the sample supply position to the overlap position, and can be detected by the detecting section.

Moreover, it is preferable for the detecting section to be formed so as to be capable of performing colorimetric measurements or electrochemical measurements.

In this case, the colorimetric measurement or electrochemical measurement can be performed on a sample that has been moved to the detecting section.

Moreover, it is preferable for the base component to be non-conductive, and for the detecting section to have an electrode system that includes a working electrode, a reference electrode, and a counter electrode that are formed on the surface of the base component at a distance from the sample supply position.

In this case, when a sample is moved from the sample supply position to the detecting section, the sample comes into contact with each one of the working electrode, the reference electrode, and the counter electrode, and an electrochemical measurement of the sample can be performed.

Moreover, it is preferable for at least one of the mutually facing portions of the sample receptacle portion and the base component to be formed such that at least a portion thereof is hydrophilic.

In this case, because the sample spreads all over the hydrophilic portion in the space formed by the sample receptacle portion and the base component, it is easy to supply the sample.

Moreover, it is preferable for supporting portions to be provided in two locations that are separated from each other such that the overlap position is sandwiched between them on the base component.

In this case, because each of the supporting portions, which are provided in two locations, support the sliding component, the sliding component can be supported stably on the base component.

Moreover, it is preferable for the supporting portion to have guide portions, and for these guide portions to be separated from each other such that the overlap position is sandwiched between them on the base component, and for the guide portions to also be provided in parallel with each other.

In this case, the sliding component can be made to slide freely alongside the two guide portions that are provided in parallel with each other.

Moreover, it is preferable for the supporting portion to have a covering portion that covers the overlap position such that a gap through which the sliding component is able to move backwards and forwards is created between the covering portion and the base component.

In this case, because the sliding component is covered by the covering portion, the sliding component is able to slide freely relative to the base component, and it is difficult for the sliding component to fall out from the supporting portion.

Moreover, it is preferable for the sliding component to have a flow stopping portion that stops the flow of the sample from the sample receptacle portion to the electrode system formed in a portion of the slide body, and for the flow stopping portion to be positioned between the overlap position and the sample supply position when the sample receptacle portion is located at the sample supply position.

In this case, because the sample is prevented from flowing to the electrode system by the flow stopping portion, it is possible to prevent the sample from entering the detecting section before the sliding component has been made to slide over the base component and, as a consequence, moving the sample from the sample supply position to the detecting section.

Moreover, it is preferable for the flow stopping portion to have a hole portion or a recessed portion that, when viewed from a normal direction of the surface of the base component, has at least a portion of an edge portion thereof that is positioned between the overlap position and the sample supply position when the sample receptacle portion is located at the sample supply position.

In this case, the flow of the sample can be stopped at the edge portion of the hole portion or recessed portion.

Moreover, it is preferable for the flow stopping portion to be formed on the sliding component so as to protrude from the sliding component in the direction of the base component when the sliding component is mounted on the base component.

In this case, when the sliding component is assembled with the base component, the sample can be blocked by the flow stopping portion so that the flow of the sample can be stopped by the flow stopping portion.

Moreover, it is preferable for the sliding component to have flow restricting portions between the slide body and the sample receptacle portion that restrict the flow of the sample from the sample receptacle portion towards the slide body.

In this case, because the flow of the sample contained in the sample receptacle portion towards the slide body is restricted, a fixed quantity of sample can be consistently contained in the sample receptacle portion.

Moreover, it is preferable for the flow restricting portion to be formed by cutting notches in a portion of the slide body adjacent to the sample receptacle portion.

In this case, the flow of a sample can be stopped by step portions which are formed by cutting notches in a portion of the slide body.

Moreover, it is preferable for a preprocessing reagent that is used in preprocessing in order to either remove or capture any interfering substances that may obstruct the detection, or to convert such interfering substances into another substance that has no effect on the detection to be placed on at least one of the sample receptacle portion and the sample supply position.

In this case, preprocessing using a preprocessing reagent is performed while a sample is contained in the sample receptacle portion at the sample supply position, and the detection is then made after the sliding component has been made to perform a sliding movement so that the sample has been moved from the sample supply position to the detecting section.

Moreover, it is preferable for at least one of the counter electrode and the reference electrode to be a silver-silver chloride electrode which employs silver and silver chloride.

In this case, it is possible to make electrochemical measurements of a sample that can be easily reproduced.

Moreover, it is preferable for there to be further provided a pair of conduction detecting electrodes that are located apart from each other and are exposed on the surface of the base component at the sample supply position, and for the pair of conduction detecting electrodes to be made conductive with each other by the sample that is supplied to the sample supply position.

In this case, when a sample is supplied to the sample supply position, because the pair of conduction detecting electrodes change to a conductive state, it is possible to detect the fact that a sample has been supplied.

Moreover, it is preferable for a surface of the conduction detecting electrodes to be hydrophilic.

In this case, it is easy for a sample to stick to the conduction detecting electrodes.

Moreover, it is preferable for the guide portions to be hydrophobic.

In this case, it is possible to prevent a sample from entering into the gap between the guide portions and the sliding component.

Moreover, it is preferable for an elongated hole that is elongated in the sliding direction in which the sliding component slides relative to the base component to be formed in the base component; and for a through hole that, when viewed from the thickness direction of the sliding component, overlaps with the elongated hole when the sliding component is being supported by the supporting portion to be formed in the sliding component.

In this case, by using a rod or the like that is inserted through the elongated hole and the through hole, the sliding direction of the sliding component can be guided in the direction in which the elongated hole extends.

Moreover, it is preferable for an oxidation-reduction enzyme and a redox mediator to be placed on at least the working electrode of the electrode system.

Moreover, it is preferable for the redox mediator to include at least one selected from ruthenium derivatives, osmium derivatives, ferricyan derivatives, ferrocene derivatives, quinine derivatives, phenothiazine derivatives, phenoxazine derivatives, phenazine derivatives, indophenol derivatives, diphenylamine derivatives, and phenol derivatives.

Moreover, it is preferable for the oxidation-reduction enzyme to include at least one selected from pyranose oxidase, L-sorbose oxidase, 1,5-AG dehydrogenase, L-sorbose dehydrogenase, and 1,5-anhydroglucitol-6-phosphate dehydrogenase.

Moreover, it is preferable for the preprocessing reagent to contain a reagent that either removes or captures glucose, or else converts glucose into another substance that has no effect on the detection.

In these cases, it is possible to create a detection device for measuring 1,5-AG that is able to perform a superior 1,5-AG measurement.

Effects of the Invention

According to the detection device of the present invention, because it is possible to move a sample from a sample supply position to an overlap position which overlaps with a detecting section simply by causing a sliding component to slide relative to a base component, multistage processing can be performed with safety and by means of a simple structure.

DETAILED DESCRIPTION OF THE INVENTION

Description of Embodiments

First Embodiment

A detection device according to a first embodiment of the present invention will now be described with reference made to FIG. 1 and FIG. 2. The detection devices in each of the following embodiments, including the present embodiment, are 1,5-AG measurement detection devices which are used for measuring 1,5-AG.

Figure 1A:
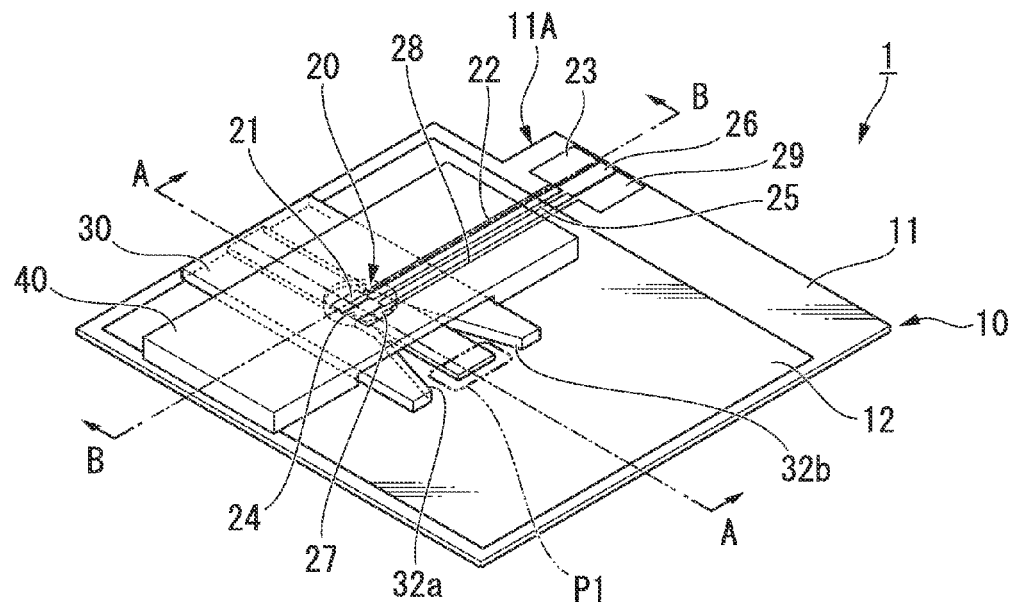
FIG. 1A is a perspective view showing a detection device according to a first embodiment of the present invention.
Figure 1B:
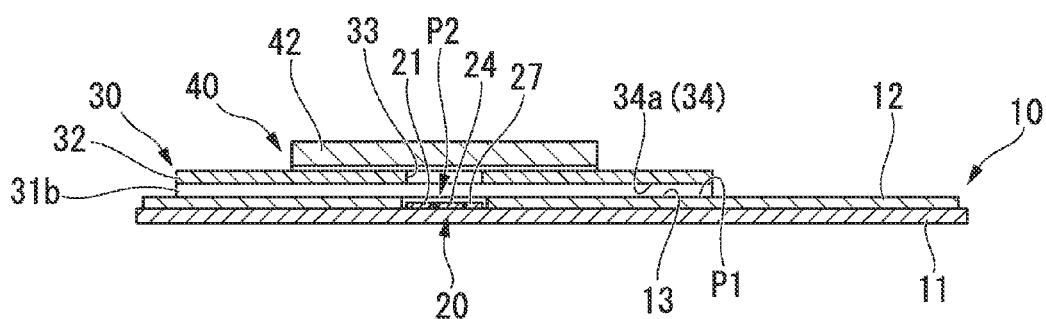
FIG. 1B is a cross-sectional view taken along a line A-A in FIG. 1A.
Figure 1C:
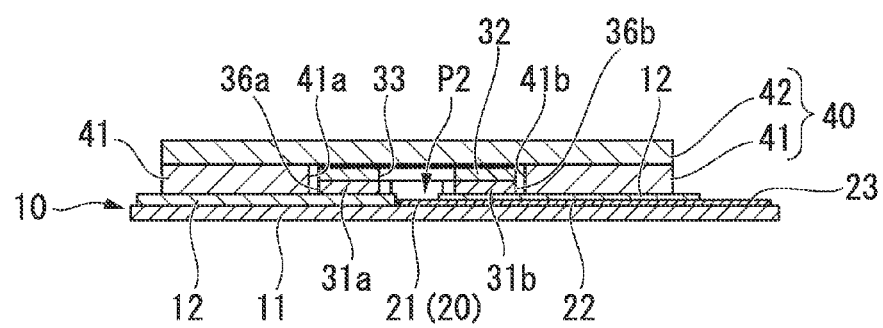
FIG. 1C is a cross-sectional view taken along a line B-B in FIG. 1A.

FIG. 1A is a perspective view showing a detection device according to the present embodiment, FIG. 1B is a cross-sectional view taken along a line A-A in FIG. 1A, and FIG. 1C is a cross-sectional view taken along a line B-B in FIG. 1A.

As is shown in FIGS. 1A through 1C, a detection device 1 is formed by a base component 10 which is formed from a non-conductive material, an electrode system (i.e., a detecting section) 20 which is formed on a surface of the base component 10, a sliding component 30 which performs sliding movements relative to the base component 10 on a surface of the base component 10, and a supporting portion 40 which supports the sliding component 30 such that it is able to slide relative to the base component 10.

The base component 10 has a substrate 11 which is formed in a plate shape, and a resist layer 12 which is laminated on top of the substrate 11.

One end portion of the substrate 11 is formed as an insertion portion 11A which is inserted into an inspection instrument. The non-conductive material which is used to form the substrate 11 is not particularly restricted as long as it is non-conductive and has the required strength, and, for example, plastic film or the like may be used. The plastic film is not particularly restricted as long as it has a high molecular compound as its primary constituent and is molded onto a film, however, examples of preferred high molecular compounds include polyethylene terephthalate (PET), polyethylene naphthalate (PEN), polycarbonate (PC), polyalylate, polyether sulfone (PES), polyimide, polyamide, polypropylene (PP), polyethylene (PE), cyclo-olefin polymers (COP), polymethyl methacrylate (PMMA), polydimethylsiloxane (PDMS), triacetyl cellulose (TAC), diacetyl cellulose (DAC), polystyrene (PS), polyurethane, polyvinyl alcohol (PVA), eval (ethylene-vinyl alcohol copolymers), polyvinyl chloride (PVC) and the like. In addition to these, it is also possible for glass and the like to be used as the material of the substrate 11, however, of the aforementioned materials, PET is very easy to handle and is, therefore, preferable for the material of the substrate 11.

The resist layer 12 is formed as a thin layer by, for example, screen printing or the like a thermosetting or UV-curable non-conductive paint onto a surface of the substrate 11. In the resist layer 12 of the present embodiment, the surface thereof that is exposed to the outside is hydrophobic. Moreover, apertures where a counter electrode 21, a working electrode 24, and a reference electrode 27 of the electrode system 20 (described below) are exposed to the outside are formed in the resist layer 12.

The electrode system 20 is formed as a thin film on a surface of the substrate 11 of the base component 10, and has the counter electrode 12, the working electrode 24, and the reference electrode 27 that are formed so as to be exposed via the aforementioned apertures.

The counter electrode 21 and the working electrode 24 are formed on the substrate 11 by a screen printing method using conductive carbon ink. Wiring portions 22 and 25, which extend as far as the insertion portion 11A, and contact electrodes 23 and 26, which are formed at the position of the insertion portion 11A and are conductive respectively with the wiring portions 22 and 25, are provided in the counter electrode 21 and the working electrode 24.

The reference electrode 27 is a silver-silver chloride electrode which is formed on the substrate 11 by a screen printing method. In the same way as the counter electrodes 21 and the working electrode 24, the reference electrode 27 has a wiring portion 28 and a contact electrode 29, and is formed so as to extend as far as the insertion portion 11A.

The contact electrodes 23, 26, and 29 are connected with the inspection instrument when the insertion portion 11A is inserted into the inspection instrument.

The area where the counter electrode 21, the working electrode 24, and the reference electrode 27 overlap on the surface of the base component 10 forms an overlap position P2 that is used to make electrochemical measurements of a test sample. A measurement reagent (not shown) that reacts with the sample and thereby makes it possible to measure the sample electrochemically is provided by a method such as dipping or spin-coating on the surface of the base component 10 within the overlap position P2 and including the surfaces of the counter electrode 21, the working electrode 24, and the reference electrode 27. It is preferable that the overlap position P2 has a shape that encloses the counter electrode 21, the working electrode 24, and the reference electrode 27 and, in the present embodiment, the overlap position P2 is formed substantially in a square shape.

The content of the measurement reagent that is used to electrochemically measure the sample may be suitably selected depending on the reaction to be generated at the overlap position P2. It is also possible when performing measurements such as those in which the generated hydrogen peroxide is to be directly detected for an oxidizing enzyme alone to be used. Moreover, it is also possible for no measurement reagent to be used when, for example, sodium ions or potassium ions or the like, which are capable of being measured without the substance being measured requiring any particular reaction, are being measured.

In the detection device 1 of the present embodiment, a redox mediator which performs the role of an intermediary in the transfer of oxidation-reduction enzymes that have a 1,5-AG oxidation potential, and of electrons that participate in the oxidation-reduction reaction is placed in the electrode system 20.

As the oxidation-reduction enzymes that have an 1,5-AG oxidation potential, it is possible to use a pyranose oxidase, an L-sorbose oxidase, a 1,5-AG dehydrogenase, an L-sorbose dehydrogenase, a 1,5-anhydroglucitol-6-phosphate dehydrogenase, and the like.

Possible redox mediators that may be used include ruthenium derivatives, osmium derivatives, ferricyan derivatives, ferrocene derivatives, quinine derivatives, phenothiazine derivatives, phenoxazine derivatives, phenazine derivatives, indophenol derivatives, diphenylamine derivatives, and phenol derivatives and the like. Specifically, [osmium (bipyridyl)$_2$ imidazoyl Cl] Cl$_2$, [osmium (bipyridyl)$_2$Cl] complexated with polyvinylimidazole, potassium ferricyanide, sodium ferricyanide, ferrocene, ferrocenemethanol, ferrocene PEG, and the like may be used.

Moreover, possible phenothiazine derivatives that may be used as the redox mediator include thionine acetate, thionine chloride, methylene blue, methylene green, 10-(carboxymethyl amino carbonyl)-3,7'-bis(dimethyl amino)-phenothiazine sodium, toluidine blue O, azure C, azure A, azure I, azure B, new methylene blue, and benzoyl leucomethylene blue, Of these, methylene blue, thionine acetate, thionine chloride, azure C, azure A, azure I, azure B, and toluidine blue O are preferable, and thionine acetate is particularly preferable.

The sliding component 30 has a slide body 32 which is formed in a plate shape, a sample receptacle portion 34 which is provided in a portion of one end of the slide body 32, and a pair of spacers 31a and 31b which are fixed to one surface of the slide body 32 in two locations that are separated from each other such that the sample receptacle portion 34 is positioned between them.

In the same way as the substrate 11, the slide body 32 is formed by a plastic film which has a high molecular compound as its primary constituent. It is preferable that PET is used as the material of the slide body 32. A through hole 33 that penetrates the slide body 32 in the plate-thickness direction thereof is formed in the vicinity of the center of the slide body 32. The shape of the through hole 33 is formed by hollowing out the slide body 32 in a circular cylinder shape whose center axis is aligned with the plate thickness direction of the slide body 32.

The sample receptacle portion 34 is set in a portion of the same plastic film as that of the slide body 32. The two sides of the portion where the sample receptacle portion 34 extends are cut off from the slide body 32 by notches (i.e., flow restricting portions) 32a and 32b which are formed in the plastic film that is used to make up the slide body 32.

A surface 34a on the side of the sample receptacle portion 34 which faces the base component 10 is hydrophilic. The hydrophilization processing to make the sample receptacle portion 34 hydrophilic may employ, for example, corona processing, plasma processing, UV/ozone processing, or frame processing or the like as surface reforming processing. It is also possible to employ a method in which a hydrophilic compound such as polyvinyl alcohol, hydroxyalkyl cellulose, or agarose is coated onto wall surfaces of the sample receptacle 34, or a method in which a silicon oxide film is formed on wall surfaces of the sample receptacle portion 34 by Itro processing.

Note that the above-described hydrophilization processing may also be suitably employed if the above-described exterior surface of the resist layer 12 of the base component 10 is to be made hydrophilic. It is also possible to form the slide body 32 from a triacetyl cellulose film, and to perform the hydrophilization processing by performing alkaline processing on the surface layer of the surface portion 34a of the sample receptacle portion 34 which faces the base component 10.

As is shown in FIGS. 1B and 1C, the spacers 31a and 31b are formed by adhering a plastic film whose thickness extends in the plate-thickness direction of the slide body 32 to the slide body 32 by means of, for example, two-sided adhesive tape.

The surfaces of the spacers 31a and 31b on the opposite side from the surface thereof that is fixed to the slide body 32 are in contact with the base component 10. The sample receptacle portion 34 and the base component 10 are separated from each other by the same distance as the thickness of the spacers 31a and 31b. Accordingly, the size of the gap created by the spacers 31a and 31b between the sample receptacle portion 34 and the base component 10 can be set to different sizes by changing the thickness of the spacers 31a and 31b. In the present embodiment, a fixed quantity of sample can be contained in the space created by the sample receptacle portion 34 and the base component 10.

Note that it is also possible for the spacers 31a and 31b to be molded integrally with the slide body 32. For example, the slide body 32 can be formed by extrusion molding or the like such that a trench portion is formed between the spacer 31a and the spacer 31b. In this case, compared with when the spacers 31a and 31b are separate bodies independent of the slide body 32, it is possible to easily form a sliding component 30 that is capable of containing a sample with a high level of precision. Moreover, if the spacers 31a and 31b are molded integrally with the slide body 32, then it is also possible to reduce the manufacturing costs when mass-producing the sliding component 30.

Moreover, other methods of molding the spacers 31a and 31b integrally with the slide body 32 that can be employed include forming holes in the slide body 32, or forming a trench by cutting the slide body 32 so that a gap for housing a sample is provided.

As is shown in FIG. 1C, the supporting portion 40 has a pair of plate-shape guide portions 41 which are fixed to the resist layer 12 of the base component 10, and a covering component 42 which spans the gap between the respective guide portions 41.

The guide portions 41 are formed by adhering a plastic film whose thickness extends in the plate-thickness direction of the base component 10 to the base component 10 by means of, for example, two-sided adhesive tape. For example, the guide portions 41 may be formed thicker than the plate-thickness of the sliding component 30 by superimposing layers of plastic film and two-sided adhesive tape. Moreover, guide surfaces 41a and 41b that extend in parallel with a direction along the surface of the base component 10 are formed in mutually facing portions of the pair of guide portions 41.

The covering component 42 is fixed to the guide portions 41, and has a gap that is slightly larger than the plate-thickness of the sliding component 30 in the direction of the plate-thickness of the base component 10, and covers the counter electrode 21, the working electrode 24, and the reference electrode 27 on the base component 10.

The sliding component 30 is inserted into the cavity portion that is formed by the guide portions 41 and the covering component 42. As a consequence of this, the sliding component 30 is guided in the direction in which the guide surfaces 41a and 41b extend, and the sliding component 30 is able to freely perform sliding movements relatively to the base component 10.

Note that in the supporting portion 40, it is also possible for the guide portions 41 and the covering component 42 to be molded integrally with each other. In this case, the supporting portion 40 can be easily mass produced. In the same way as in the above-described example of the integral molding of the sliding component 30, methods that may be employed to integrally mold the supporting portion 40 include extrusion molding, cutting and the like.

In a state in which the sliding component 30 is supported by the supporting portion 40 and has been placed on top of the base component 10, when the through hole 33 in the sliding component 30 is located in the overlap position P2 and is overlapping with the electrode system 20, the positional relationship of the sample receptacle portion 34 is such that it is positioned outside the cavity that is covered by the covering component 42. At this time, the position where the resist layer 12 and the sample receptacle portion 34 appear to be mutually superimposed with each other when they are viewed from the plate-thickness direction of the base component 10 is set as a sample supply position P1 where a sample is supplied to the sample receptacle 34.

Namely, when the sample receptacle portion 34 is located at the sample supply position P1, edge portions of the through hole 33 that are located on the sample receptacle portion 34 side are positioned between the overlap position P2 and the sample supply position P1. As a result of this, when the sample receptacle portion 34 is positioned at the sample supply position P1, the sample that is contained in the sample receptacle portion 34 is stopped at a boundary formed by the edge portion of the through hole 33 that is located on the sample receptacle portion 34 side, so that the sample is prevented from entering inside the overlap position P2.

In this manner, in the present embodiment, the edge portion of the through hole 33 that is located on the sample receptacle portion 34 side forms a flow stopping portion that stops any flow movement of the sample.

A preprocessing reagent 13 is fixed in position on the surface of the resist layer 12 that is located within the area of the sample supply position P1. The preprocessing reagent 13 is used to either decompose, remove, or capture any glucose within the sample, as glucose is a substance that interferes with the 1,5-AG measurement, or to elicit a preprocessing reaction to convert such glucose into another substance that has no effect on the electrochemical measurement. Methods employed to fix the preprocessing reagent 13 in position include coating and drying, screen-printing, and the like. Enzymes having an action of either decomposing or converting glucose are contained in the preprocessing reagent 13 of the present embodiment.

Specifically, if the glucose is to be oxidized, then examples of the preprocessing reagent 13 include glucose oxidase, and compounds of glucose dehydrogenase together with nicotinamide adenine dinucleotide (NAD) or nicotinamide adenine dinucleotide phosphate (NADP) as a coenzyme. If the glucose is to be phosphorylated, then examples of the preprocessing reagent 13 include hexokinase or glucokinase or the like.

Note that it is to be understood that the composition of the preprocessing reagent 13 may be appropriately altered in accordance with the required preprocessing reaction if the method used to measure the sample, or the subject substance that is to be measured are different from those described above. The contents of the preprocessing reaction are also not particularly restricted, and in addition to various reactions such as decomposition, removal, and conversion, a variety of preprocessing reactions such as trapping (i.e., capturing) by means of ion absorption, affinity absorption, or absorption by microbeads using a boric acid compound may be performed, insofar as they are capable of being elicited using the detection device 1.

An operation which is performed when a 1,5-AG measurement is made using the detection device 1 having the above-described structure will now be described with reference made to FIGS. 2A through 2C. Hereinafter, a description is given of a case when the user who is using the detection device 1 measures the 1,5-AG by means of the detection device 1 using a whole blood sample taken from their own body. Note that users who may use the detection device 1 are not limited to the aforementioned type of user.

The detection device 1 is prepared when the sample receptacle portion 34 is positioned at the sample supply position P1. The user sets the detection device 1 in the inspection instrument by inserting the insertion portion 11A of the detection device 1 in the inspection instrument.

Figure 2A:
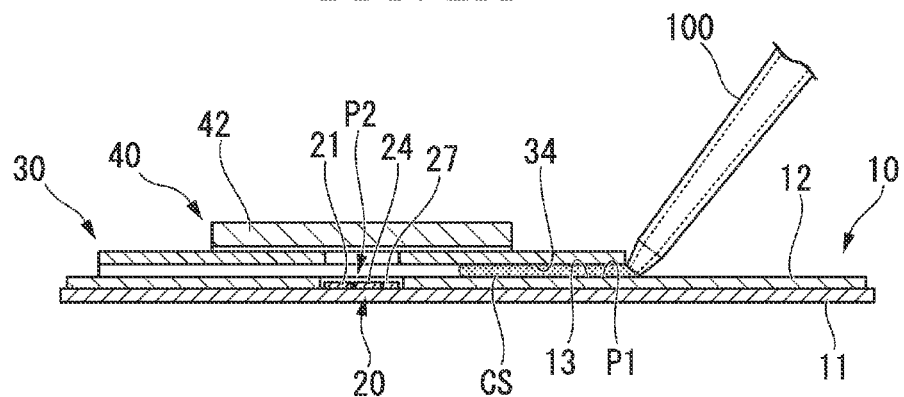
FIG. 2A is a cross-sectional view of the detection device when the detection device is being used.

Next, as is shown in FIG. 2A, the user drips a whole blood sample (i.e., a sample) CS obtained from their fingertip or the like onto the sample supply position P1, and makes it flow into the space between the resist layer 12 of the base component 10 and the sample receptacle portion 34. As a result, a reaction is started to decompose or convert or the like the glucose within the whole blood sample CS by means of the pre-processing reagent 13 which has been fixed in the sample supply position P1.

When a predetermined time has elapsed with the whole blood sample CS remaining stationary in the sample supply position P1, the decomposition, removal, or capture of the glucose within the whole blood sample CS, or else the conversion thereof to another substance that will not affect the electrochemical measurement is completed, and the whole blood sample CS becomes a measurement sample (i.e., a sample) S that has completed measurement preparations.

Figure 2B:
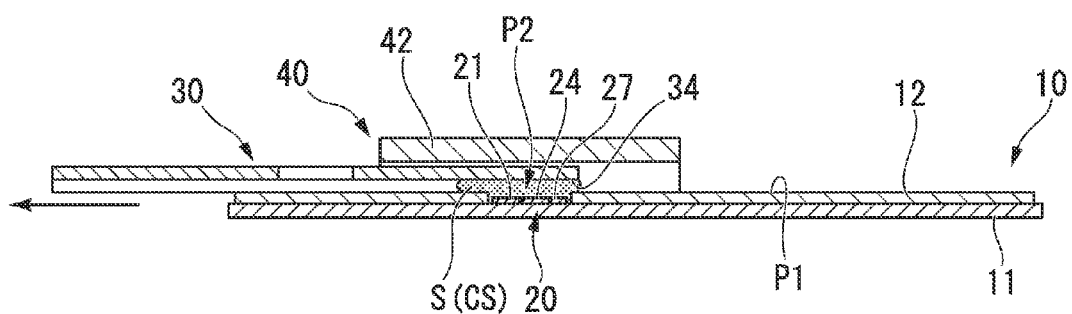
FIG. 2B is a cross-sectional view of the detection device when the detection device is being used.
Figure 2C:
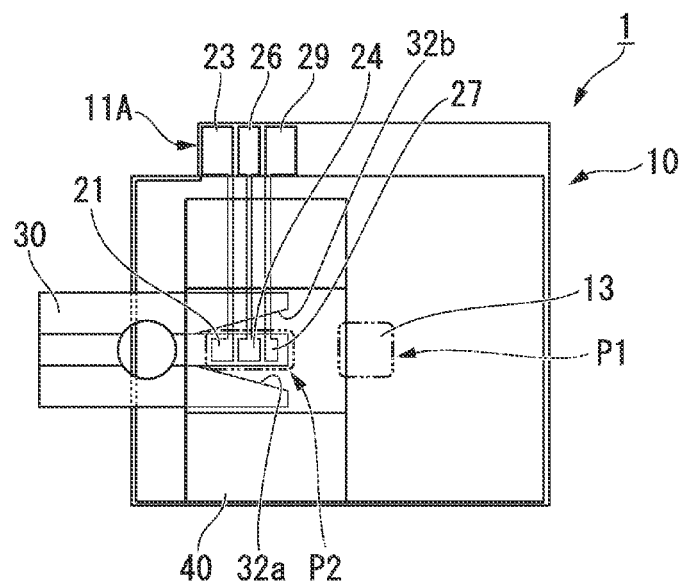
FIG. 2C is a cross-sectional view of the detection device when the detection device is being used.

As shown in FIGS. 2B and 2C, the user then slides the sliding component 30 relative to the base component 10, so that the sample receptacle portion 34 is moved to the overlap position P2. As a result, the measurement sample S follows the movement of the sliding component 30 and is moved over the resist layer 12 of the base component 10. The measurement sample S then reaches the overlap position P2, and comes into contact with the counter electrode 21, the working electrode 24, and the reference electrode 27 of the electrode system 20.

The measurement sample S that has been introduced to the overlap position P2 instigates a known reaction such as an oxidation-reduction reaction with the measurement reagent which has been placed at the overlap position P2. Voltage is then applied from the inspection instrument to the electrode system 20 of the detection device 1, and the 1,5-AG concentration is measured by measuring the value of the current flowing in the electrode system 20. Note that an amperometry method (i.e., a current measurement method), a coulometry method (i.e., an electricity quantity measurement method), a phase sweep method, or a cyclic voltammetry method or the like may be suitably employed as the electrochemical measurement method.

According to the detection device 1 of the present embodiment, simply by sliding the sliding component 30 relative to the base component 10 after the preprocessing reaction has taken place at the sample supply position P1, the measurement sample (i.e., the sample) S is able to reach the overlap position P2 and the reaction required for the electrochemical measurement can be generated. Because of this, multistage processing can be performed safely by means of a simple structure without a complex flow path structure being required.

Moreover, because the surface of the sample receptacle portion 34 on the side thereof that faces the base component 10 is hydrophilic, the sample that is supplied between the sample receptacle portion 34 and the base component 10 spreads out inside the sample receptacle portion 34. Because of this, it is possible to easily supply a fixed quantity of sample to the sample receptacle portion 34.

Furthermore, because the sample can perform the sliding movement while it is adhering to the hydrophilic surface of the sample receptacle portion 34, it is difficult for the sample to overflow from the sample receptacle portion 34 while the sliding component 30 is performing the sliding movement.

Moreover, because the supporting portion 40 is provided in two locations that are separated from each other such that the overlap position P2 lies between them on the base component 10, the sliding portion 40 is able to support the sliding component 30 at two mutually separated points. Because of this, the sliding portion 40 is able to stably support the sliding component 30.

Moreover, because the guide portions 41 of the supporting portion 40 have the guide surfaces 41a and 41b which are provided in parallel with each other, the sliding component 30 can be moved precisely in a straight line so as to follow the guide portions 41.

Moreover, the covering component 42 (i.e., a covering portion) is provided on the supporting portion 40 so that a gap where the sliding component 30 can be moved forwards and backwards is formed between the covering component 42 and the base component 10. Because of this, the sliding component 30 is able to perform sliding movements while being prevented from dropping out from the supporting portion 40.

Moreover, a flow stopping portion is formed by the through hole 33 which is formed penetrating the slide body 32 of the sliding component 30. Because of this, the sample can be restricted by the through hole 33 from flowing to the electrode system 20, so that the whole blood sample CS can be restricted from moving forward to the position of the electrode system 20 before the sample has moved from the sample supply position P1 to the overlap position P2, and the sample can be prevented from reaching the electrode system 20 before the preprocessing reaction has ended.

Moreover, because the notches 32a and 32b (i.e., flow restricting portions) are formed between the slide body 32 and the sample receptacle portion 34, the sample contained in the sample receptacle portion 34 can be restricted from flowing onto the slide body 32. As a result, a fixed quantity of sample can be stably contained in the sample receptacle portion 34.

Moreover, because the reference electrode 27 is a silver-silver chloride electrode which employs silver and silver chloride, easily reproducible electrochemical measurements can be performed on the sample.

Second Embodiment

Next, a detection device according to a second embodiment of the present invention will be described with reference made to FIG. 3A through FIG. 4B. Note that the same symbols are used for component elements that are the same as in the detection device 1 of the above-described first embodiment, and any duplicated description thereof is omitted.

A detection device 2 of the present embodiment differs from the above-described the detection device 1 in the shape of the sliding component 30 and the supporting portion 40 which are located on the base component 10.

Figure 3A:
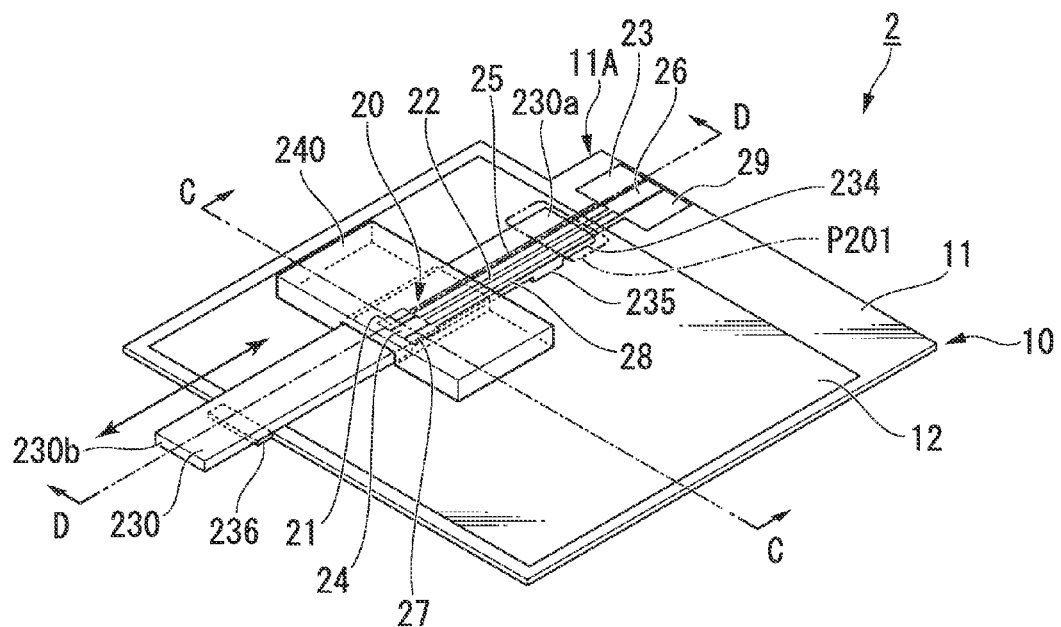
FIG. 3A is a perspective view showing a detection device according to a second embodiment of the present invention.
Figure 3B:
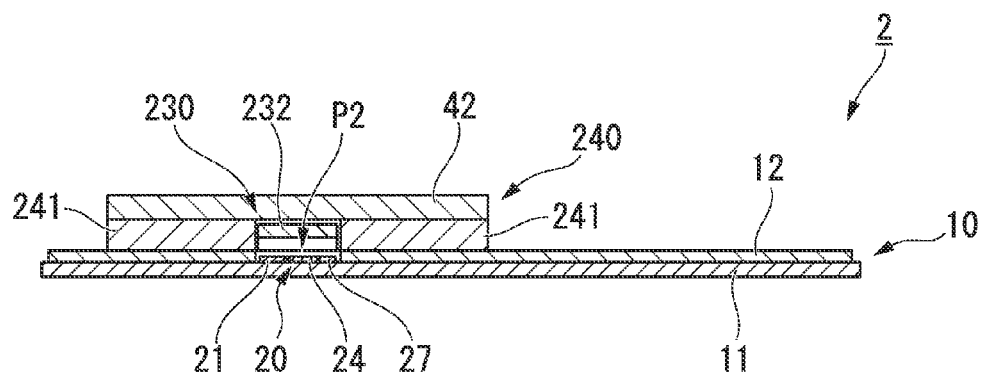
FIG. 3B is a cross-sectional view taken along a line C-C in FIG. 3A.
Figure 3C:
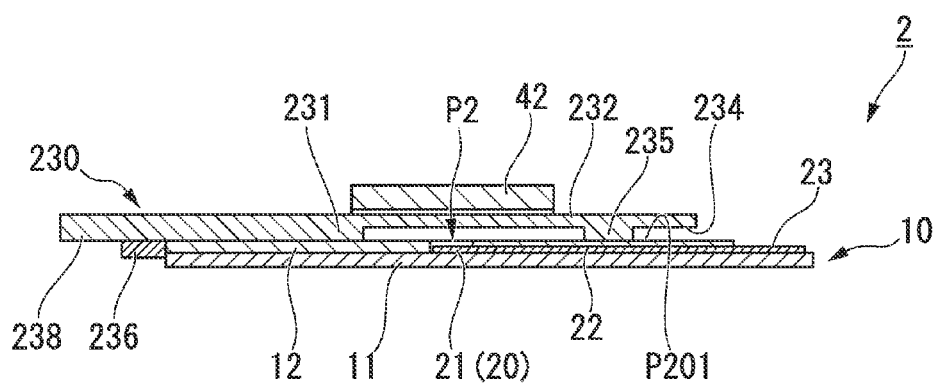
FIG. 3C is a cross-sectional view taken along a line D-D in FIG. 3A.

FIG. 3A is a perspective view showing the detection device 2 of the present embodiment. FIG. 3B is a cross-sectional view taken along a line C-C in FIG. 3A. FIG. 3C is a cross-sectional view taken along a line D-D in FIG. 3A. As shown in FIGS. 3A through 3C, the detection device 2 is provided with a sliding component 230 in place of the sliding component 30, and with a supporting portion 240 in place of the supporting portion 40.

The sliding component 230 has a slide body 232 that is formed substantially in a plate shape, and has a distal end 230a and a base end 230b. A sample receptacle portion 234, a flow stopping portion 235, a spacer 231, a stopper portion 236, and a gripping portion 238 are formed in this sequence from the distal end to the base end on the slide body 232.

In the same way as the sample receptacle portion 34 illustrated in the above-described first embodiment, the sample receptacle portion 234 is formed in a square shape that is large enough for it to overlap with each of the counter electrode 21, the working electrode 24, and the reference electrode 27 of the electrode system 20.

The flow stopping portion 235 is formed by a plastic film that is adhered by two-sided adhesive tape to the slide body 232 at the base end side of the sample receptacle portion 234, and protrudes in the direction of the base component 10. Moreover, the surface of the flow stopping portion 235 on the opposite side from the surface thereof that is adhered to the slide body 232 is in contact with the resist layer 12 of the base component 10. At this time, a gap that is used to contain a sample is created between the sample receptacle portion 234 and the resist layer 12.

In the same way as the flow stopping portion 235, the spacer 231 is formed by a plastic film that is adhered by means of two-sided adhesive tape to the slide body 232, and is located on the base end side of the flow stopping portion 235 at a distance from the flow stopping portion 235.

The stopper portion 236 is provided adjacent to the base end side of the spacer 231, and is formed so as to protrude further on the base component 10 side than the slide body 232 of the sliding component 230. The stopper portion 236 is formed such that it is able to abut against the edge of the base component 10, and the positional relationship between the sliding component 230 and the base component 10 when the stopper portion 236 is abutted against the edge of the base component 10 is such that the overlap position P2 is located between the flow stopping portion 235 of the sliding component 230 and the spacer 231, Moreover, the electrode system 20 and the sliding component 230 are separated from each other in the thickness direction of the base component 10.

The gripping portion 238 is provided such that, when the stopper portion 236 is in a positional relationship in which it is abutting against the edge of the base component 10, the gripping portion 238 extends outwards so as to protrude beyond the edge of the base component 10.

The supporting portion 240 has a pair of guide portions 241 that are formed extending in parallel with each other over the surface of the base component 10 in a perpendicular direction relative to the direction in which the guide portions 41 described in the first embodiment extend. The covering component 42 is fixed to the guide portions 241.

In the detection device 2 of the present embodiment, instead of the sample supply position P1, a sample supply position P201 is set. The location of the sample supply position P201 is set on the surface of the base component 10 such that, when the stopper portion 236 is abutting against the edge of the base component 10, the base component 10 and the sample receptacle portion 234 overlap with each other in the thickness direction of the sliding component 230.

Figure 4A:
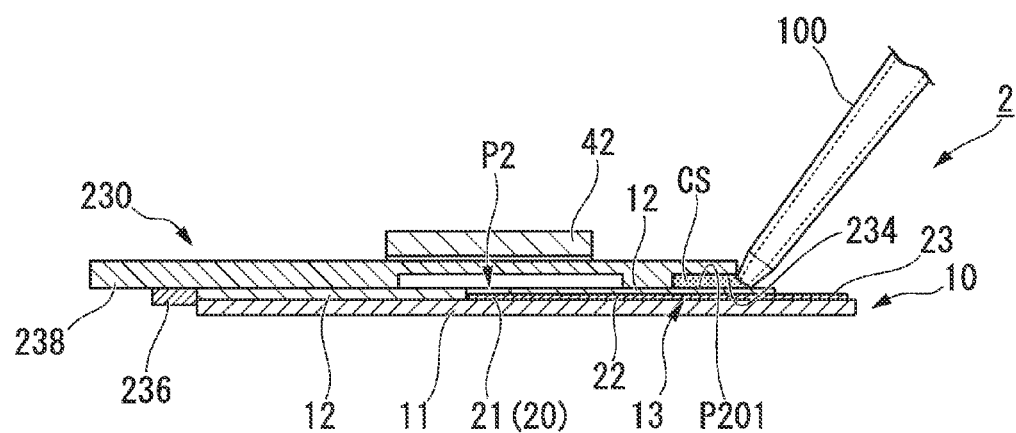
FIG. 4A is a cross-sectional view of the detection device when the detection device is being used.
Figure 4B:
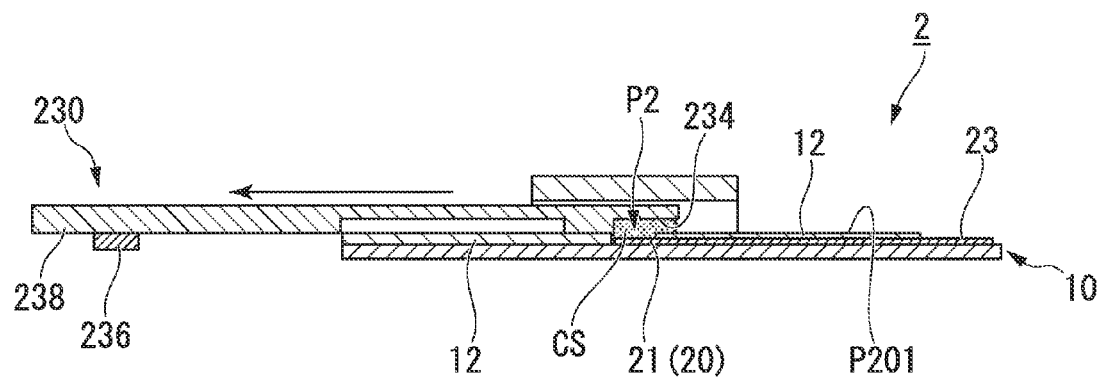
FIG. 4B is a cross-sectional view of the detection device when the detection device is being used.

An operation which is performed when a 1,5-AG measurement is made using the detection device 2 having the above-described structure will now be described with reference made to FIGS. 4A through 4C.

The detection device 2 is prepared when the sample receptacle portion 234 is positioned at the sample supply position P201. In this state, the user sets up the detection device 2 by inserting the insertion portion 11A of the detection device 2 in the inspection instrument.

The user then performs the same type of operation as the operation to supply the whole blood sample CS to the sample supply position P1 of the detection device 1 described in the first embodiment, resulting in the whole blood sample CS being supplied to the sample supply position P201. As a result, in the same way as in the first embodiment, a reaction by the pre-processing reagent is started in the sample supply position P201.

When the reaction by the preprocessing reagent has continued for a predetermined time in the sample supply position P201, in the same way as in the detection device 1 of the first embodiment, the whole blood sample CS becomes a measurement sample (i.e., a sample) S that has completed measurement preparations. Once the reaction by the preprocessing reagent has ended, the user grips the gripping portion 238 of the sliding component 230, and moves the sample receptacle portion 234 to the overlap position P2.

When the sample receptacle portion 234 is in the overlap position P2, the measurement sample S is in contact with the electrode system 20. Here, in the same way as in the above-described first embodiment, voltage is applied from the inspection instrument to the electrode system 20 of the detection device 2, and the 1,5-AG concentration is measured by measuring the value of the current flowing in the electrode system 20.

In the detection device 2 of the present embodiment as well, simply by sliding the sliding component 30 relative to the base component 10 after the preprocessing reaction has taken place at the sample supply position P201, the sample is able to reach the overlap position P2 and the reaction required for the electrochemical measurement can be generated. Because of this, multistage processing can be performed safely by means of a simple structure without a complex flow path structure being required.

Moreover, because the stopper portion 236 is formed on the sliding component 230, when the positional relationship between the stopper portion 236 and the base component 10 is such that they are abutting against each other, the sample receptacle portion 234 is positioned at the sample supply position P201. Because of this, it is possible to limit any erroneous operations and erroneous positioning when the sliding component 30 and the base component 10 are being combined together in order to measure the sample using the detection device 1

Third Embodiment

Figure 5A:
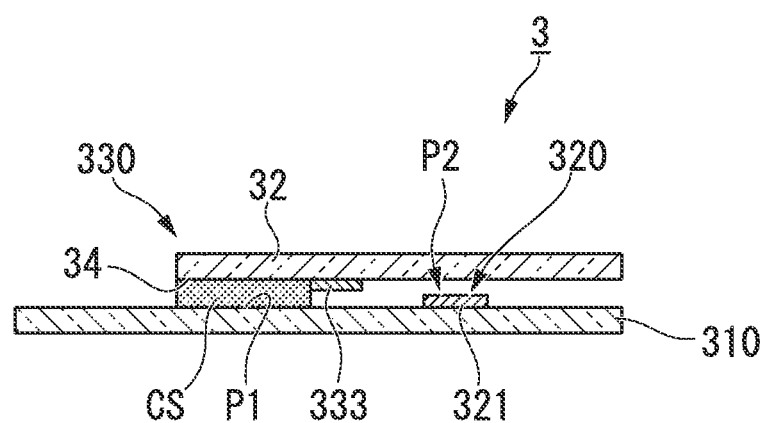
FIG. 5A is a cross-sectional view showing the structure of a detection device according to a third embodiment of the present invention.

Next, a detection device according to a third embodiment of the present invention will be described with reference made to FIGS. 5A and 5B. Note that the same symbols are used for component elements that are the same as in the detection devices of the above-described respective embodiments, and any duplicated description thereof is omitted, FIG. 5A is a cross-sectional view showing a detection device 3. As is shown in FIG. 5A, the structure of the detection device 3 differs from that of the detection device 1 of the first embodiment in that the detection device 3 is provided with a base component 310 in place of the base component 10, an optical measuring section 320 in place of the electrode system 20, and a sliding component 330 in place of the sliding component 30.

The base component 310 is a plate-shaped component that is formed such that light can be transmitted through it, and the entire surface thereof is formed so as to be transparent (including substantial transparency).

The optical measuring section 320 is formed having a light-emitting substrate layer 321 on a portion of the base component 310. The light-emitting substrate layer 321 is a film to which the measurement reagent described in the first embodiment (not shown) and a chromogen (described below) has been fixed, and that is adhered to the base component 310.

Examples of the chromogenic substrate that is used to detect light absorption include, in the case of an oxidizing chromogenic substrate, the following independently used chromogens. Namely, N-carboxymethyl amino carbonyl 4,4'-bis(dimethylamino)diphenylamine sodium salt (DA64), 10-carboxymethyl amino carbonyl 3,7-bis(dimethylamino) phenothiazine sodium salt (DA67), bis[3-bis(4-chlorophenyl)-methyl-4-dimethyl amino phenyl]amine (BCMA), bis [3-bis(4-chlorophenyl)-methyl-4-carboxyethyl amino phenyl]amine, 10-N-methylcarbamoyl-3,7-dimethyl amino-10H-phenothiazine (MCDP), 10-N-carboxymethyl carbamoyl-3,7-dimethyl amino-10H-phenothiazine (CCAP), 3,3',5, 5'-tetramethyl benzidine (TMBZ), N,N,N',N', N'',N''-hexa (3-sulfopropyl) 4,4',4''-triamino-triphenylmethane hexasodium salt (TPM-PS), and the like may be used.

Moreover, examples of couplers that are used for the coupling chromogen include 4-aminoantipyrine (4AA), 3-methyl-2-benzothiazolinone hydrazone (MBTH) and amino diphenyl-based compounds (NCP), while examples of a Trinder's reagent include N-ethyl-N-(3-methylphenyl)-N'-succinyl ethylenediamine (E-MSE), and N-rthyl-N-(2-hydroxy-3-sulfopropyl)-3-methoxyaniline (TOOS), and the like.

Moreover, in the case of a reduced chromogenic substrate, examples of the chromogen include 2-(4-iodophenyl)-3-(4-nitrophenyl)-5-phenyl-2H-tetrazolium chloride (INT), 3-(4, 5-dimethyl-2-thiazole)-2,5-diphenyl-2H-tetrazolium bromide (MTT), 3,3'-[3,3'-dimethoxy-(1,1'-biphenyl)-4,4'-diyl]-bis[2-(4-nitrophenyl)-5-phenyl-2H-tetrazolium chloride] (NTB), 2-(4-iodophenyl)-3-(4-nitrophenyl)-5-(2,4-disulfophenyl)-2H-tetrazolium 1 sodium salt (WST-1), 2-(4-iodophenyl)-3-(2,4-dinitrophenyl)-5-(2,4-disulfophenyl)-2H-tetrazolium 1 sodium salt (WST-3), and the like. Note that in the present embodiment, of these compounds, preferable chromogens are those that have a large mol light absorption coefficient in long wavelengths, and compounds that have deposition properties are particularly preferable.

The area of the base component 310 that overlaps with the optical measuring section 320 forms the overlap position P2 in the same way as in the detection device 1 of the first embodiment.

The sliding component 330 has the slide body 32, the sample receptacle portion 34 which is provided at one end of the slide body 32, and a flow stopping portion 333 which is provided on the base component 310 side of the slide body 32 so as to be positioned between the sample supply position P1 and the overlap position P2 when the sample receptacle portion 34 is located at the sample supply position P1. In the present embodiment, hydrophilization processing is performed on the surface of the sample receptacle portion 34 that faces the base component 310 in order to make the hydrophilicity thereof greater relatively than that of the flow stopping portion 333.

Hydrophobization processing is performed on the surface of the slide body 32, so that the flow stopping portion 333 forms an area having a lower degree of hydrophilicity relatively than that of the sample receptacle portion 34. Because of this, a sample (for example, the whole blood sample CS) contained in the sample receptacle portion 34 flows so as to spread over the entire sample receptacle portion 34, and stops at the boundary formed by the flow stopping portion 333.

Figure 5B:
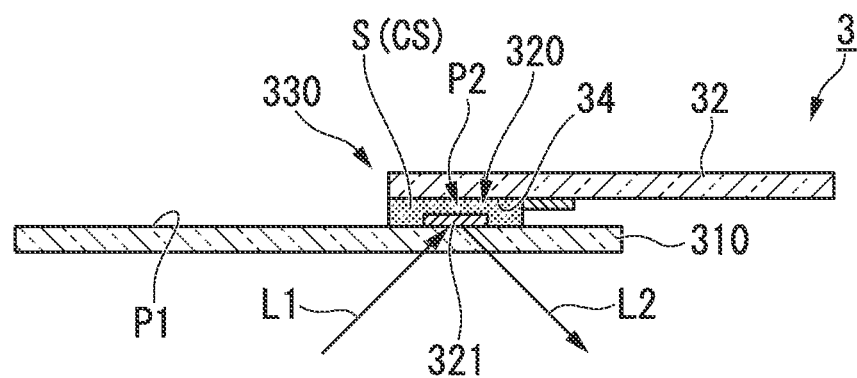
FIG. 5B is a cross-sectional view showing the structure of the detection device according to the embodiment.

FIG. 5B is a cross-sectional view showing an operation when the detection device 3 is put to use. As is shown in FIG. 5B, in the same way as the above-described detection device 1, in the detection device 3 of the present embodiment as well, the whole blood sample CS which is supplied to the sample supply position P1 does not reach the overlap position P2 unassisted, but instead reaches the overlap position P2 as a result of the sliding component 330 being made to perform a sliding movement.

Here, measurement light L1 is irradiated onto the optical measuring section 320 by an inspection instrument (not shown). In the present embodiment, the measurement light is visible light, and long wavelength light is preferable for the measurement light. The measurement light L1 is reflected by the optical measuring section 320, and reflected light L2 created from the measurement light L1 enters a measuring portion (not shown) of the inspection instrument. In the inspection instrument, colorimetric measurement is performed in order to compare the color of the reflection light L2 with an internal reference, thereby enabling the 1,5-AG concentration to be measured.

In the present embodiment, as a result of the optical measuring section 320 being provided in the detecting section, the concentration of 1,5-AG can be measured by colorimetric measurement. In the present embodiment as well, simply by sliding the sliding component 330 relative to the base component 310 after the preprocessing reaction has taken place at the sample supply position P1, the sample is able to reach the overlap position P2 and the reaction required for the colorimetric measurement can be achieved. Because of this, multistage processing can be performed safely by means of a simple structure without a complex flow path structure being required.

Modified Example 1

Hereinafter, a modified example of the detection device 3 of the above-described third embodiment will be described.

Figure 6A:
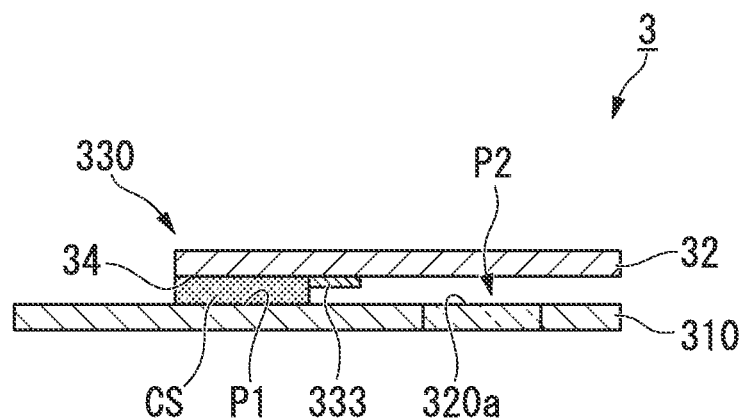
FIG. 6A is a cross-sectional view showing the structure of the detection device according to a modified example of the embodiment.
Figure 6B:
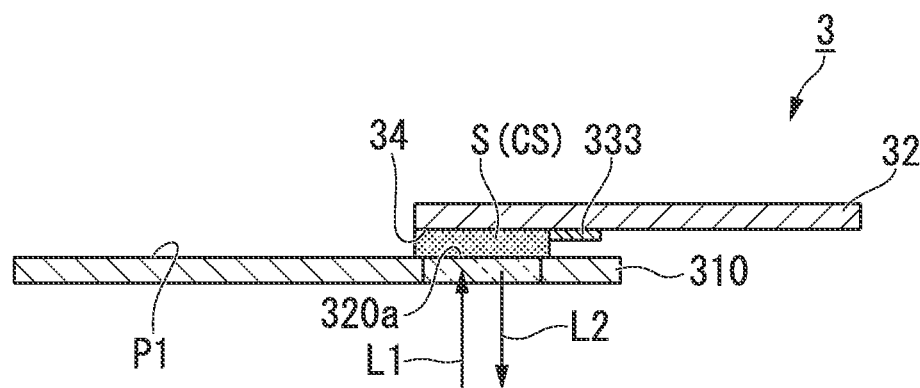
FIG. 6B is a cross-sectional view showing the structure of the detection device according to a modified example of the embodiment.

FIGS. 6A and 6B are cross-sectional views showing the detection device of the present modified example. The detection device 3 of the present modified example has an optical measuring section 320a in place of the optical measuring section 320.

The base component 310 is formed so as to be transparent (including substantial transparency) in the portion where the optical measuring section 320a is located.

In the optical measuring section 320a, the measurement reagent and chromogen described in the foregoing third embodiment are fixed in place by being directly coated onto the position of the detecting section on the surface of the base component 310. In the present modified example as well, the area of the surface of the base component 310 that overlaps with the optical measuring section 320a forms the overlap position P2 in the same way as in the detection device 1 of the first embodiment.

In this type of structure as well, in the same way as in the above-described third embodiment, it is possible to perform colorimetric measurement on a sample.

Note that in the present embodiment, an example of a structure in which the reflection light L2, which is created when the measurement light L1 is reflected by the optical measurement section 320a, is measured is described, however, it is also possible for the slide body 32 to be formed from a transparent material, and for the colorimetric measurement to be made by receiving the transmitted light from the measurement light L1 that has been transmitted through the base component 310, the measurement sample S, and the slide body 32.

Hereinafter, a modified example of the connecting structure between the supporting portion and the sliding component that can be used in each of the above-described embodiments will be described.

Modified Example 2

Figure 7:
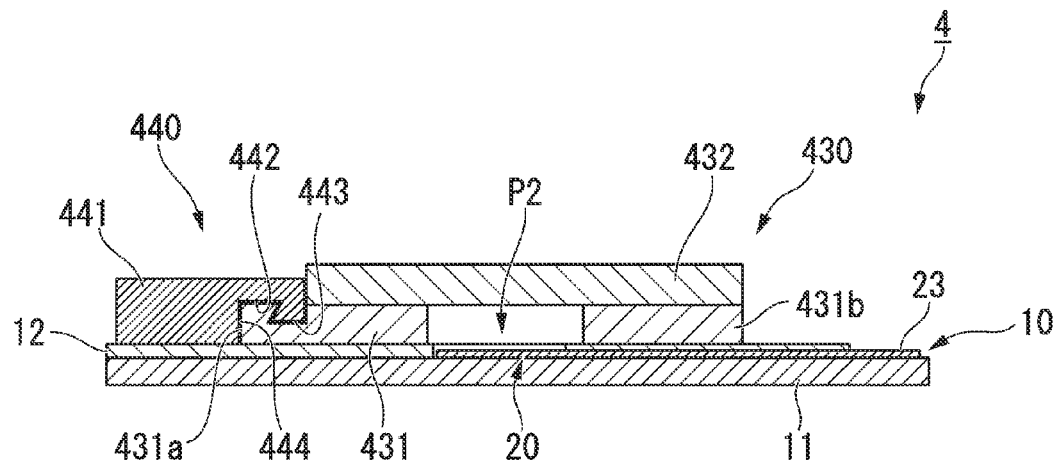
FIG. 7 is a cross-sectional view showing the structure of a modified example of the detection device of the present invention.

FIG. 7 is a cross-sectional view showing the structure of a detection device 4 of the present modified example.

In the present modified example, a supporting portion 440 is provided in place of the supporting portion 40 on the resist layer 12 of the base component 10. In addition, in place of the sliding component 30, a sliding component 430 is engaged with the supporting portion 440.

Unlike the supporting portion 40, the supporting portion 440 is only provided on one side of the sliding component 430. In addition, the supporting portion 440 supports the sliding component 430 such that it is able to slide by means of step portions 442 and 443, which are formed in a claw shape, and by means of a guide portion 444, which is formed extending in the depth direction as seen by a person looking at the drawing in FIG. 7.

In this type of structure as well, when the sliding component 430 is performing a sliding movement relative to the base component 10 from the sample supply position P1 to the overlap position P2, the sliding component 430 does not become unattached from the supporting portion 440. As a result of this, in the same way as in the above described embodiments, a sample can be moved from the sample supply position P1 to the overlap position P2.

Figure 8:
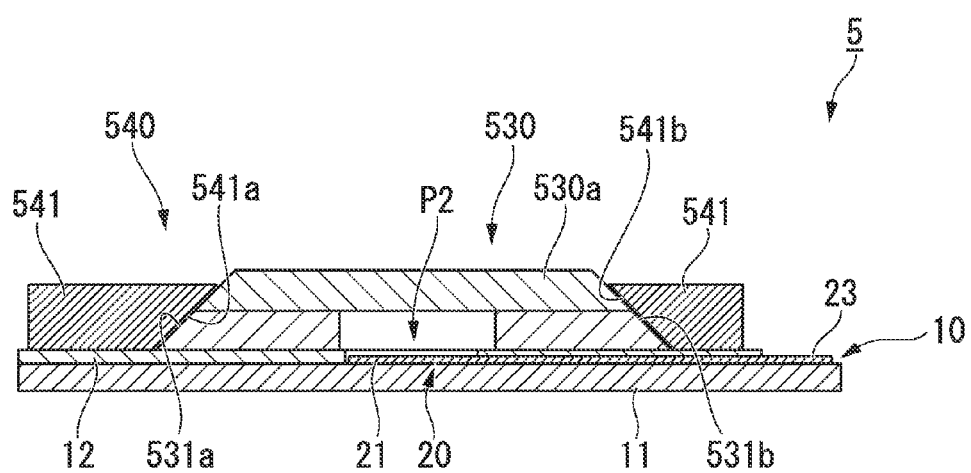
FIG. 8 is a cross-sectional view showing the structure of another modified example of the detection device of the present invention.

Note that the shape of the engaging portion between the supporting portion and the sliding component is not limited to the above-described claw shape, and, as is shown in FIG. 8, it is also possible to provide, in place of the sliding component 30, a sliding component 530 that has edge portions 531a and 531b that are formed in a sloping configuration so as to extend in the direction of the sliding movement, and, in place of the supporting portion 40, a supporting portion 540 that has a pair of supporting components 541 that are located apart from each other such that the sliding component 530 is positioned between them. In addition, the supporting components 541 have sloping portions 541a and 541b that are formed so as to slope at the same angle as the sloping angle of the edge portions.

In this case, as a result of the slopes that are formed on the edge portions 531a and 531b of the sliding component 530 being supported on the sloping portions 541a and 541b, the supporting portion 540 is able to support the sliding component 530 such that it is able to slide relative to the base component 10. Moreover, because the slope of the sloping portions 541a and 541b is such that their surfaces face towards the base component 10, it is possible to prevent the edge portions 431a and 431b, which are in contact with the sloping portions 541a and 541b, from being lifted upwards in the thickness direction of the base component 10.

Modified Example 3

Hereinafter, a modified example of the structure of the electrode system 20 will be described.

Figure 9:
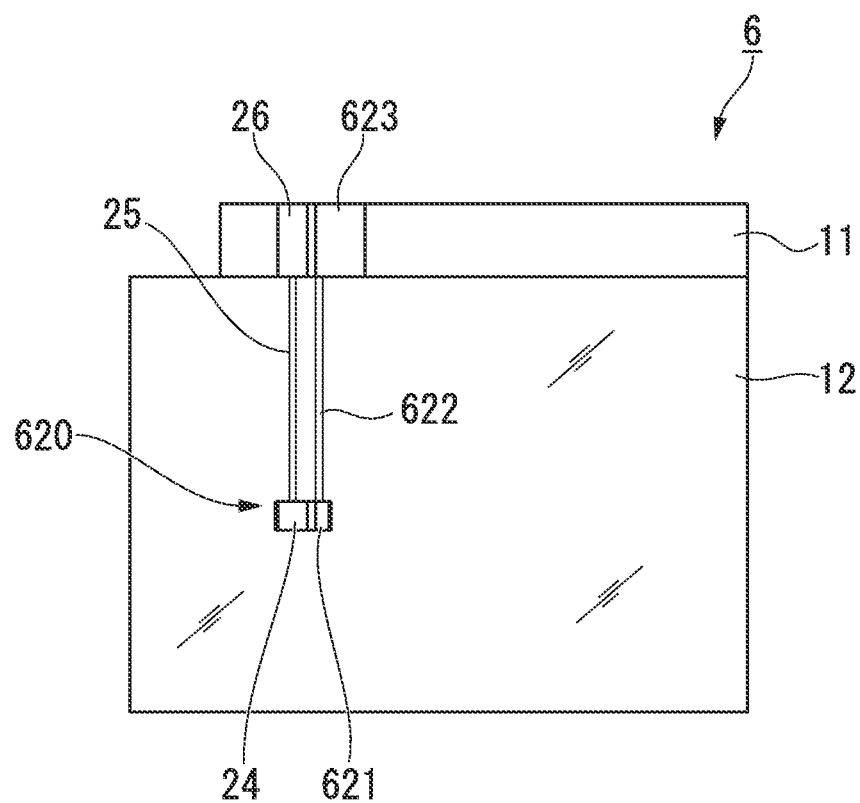
FIG. 9 is a frontal view showing the structure of a portion of yet another modified example of the detection device of the present invention.

FIG. 9 is a front view showing the structure of a portion of the detection device of the present modified example. As is shown in FIG. 9, a detection device 6 has an electrode system 630 in place of the electrode system 20.

The electrode system 620 does not have the counter electrode 21, the wiring portion 22, or the contact electrode 23, but instead has a counter electrode/reference electrode 621, which combines the functions of the counter electrode 21 with the functions of the reference electrode 27, a wiring portion 622, and a contact electrode 623.

In the present modified example, the counter electrode/reference electrode 621 is a silver-silver chloride electrode, namely, the counter electrode and the reference electrode are formed by a single silver-silver chloride electrode. In this type of structure as well, in the same way as in the detection devices 1 and 2 of the above-described first and second embodiments, it is possible to electrochemically measure a sample.

Fourth Embodiment

Next, a detection device 7 of a fourth embodiment of the present invention will be described with reference made to FIG. 10A through FIG. 12B.

Figure 10A:
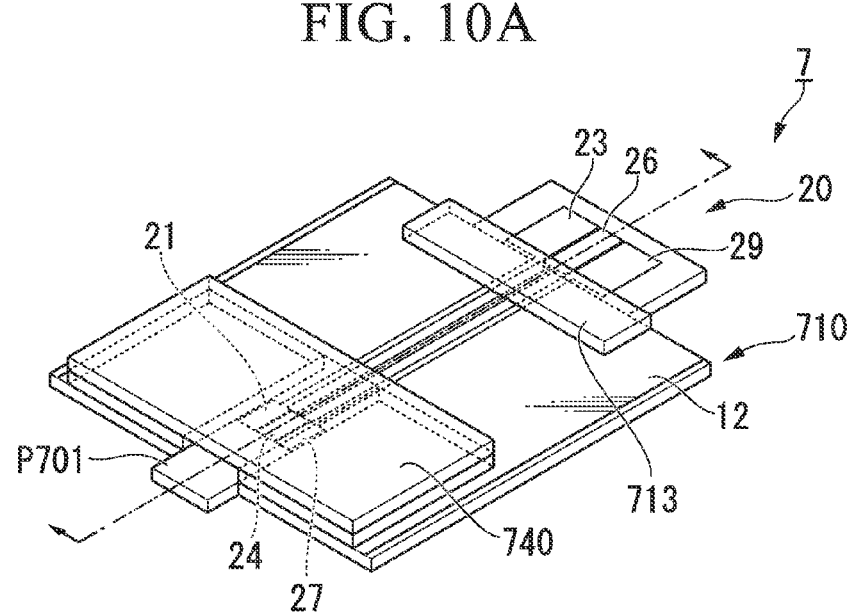
FIG. 10A is a perspective view showing the structure of a portion of a detection device according to a fourth embodiment of the present invention.
Figure 10B:
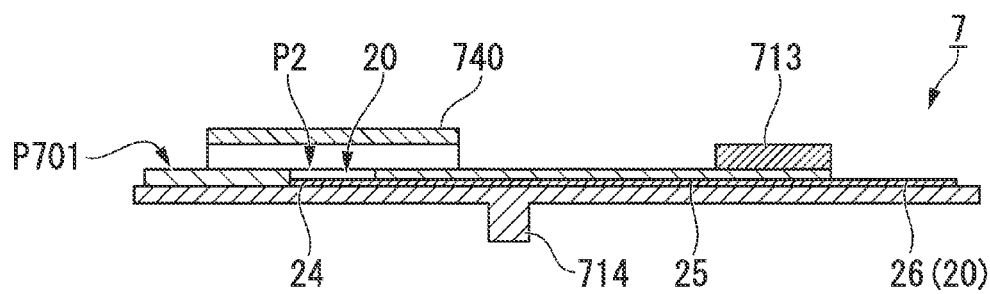
FIG. 10B is a cross-sectional view showing the structure of a portion of the detection device.
Figure 10C:
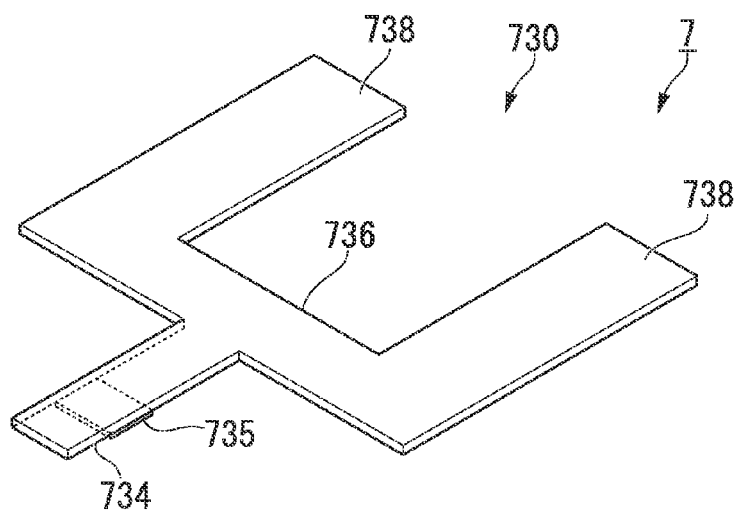
FIG. 10C is a perspective view showing the structure of a portion of the detection device.
Figure 11A:
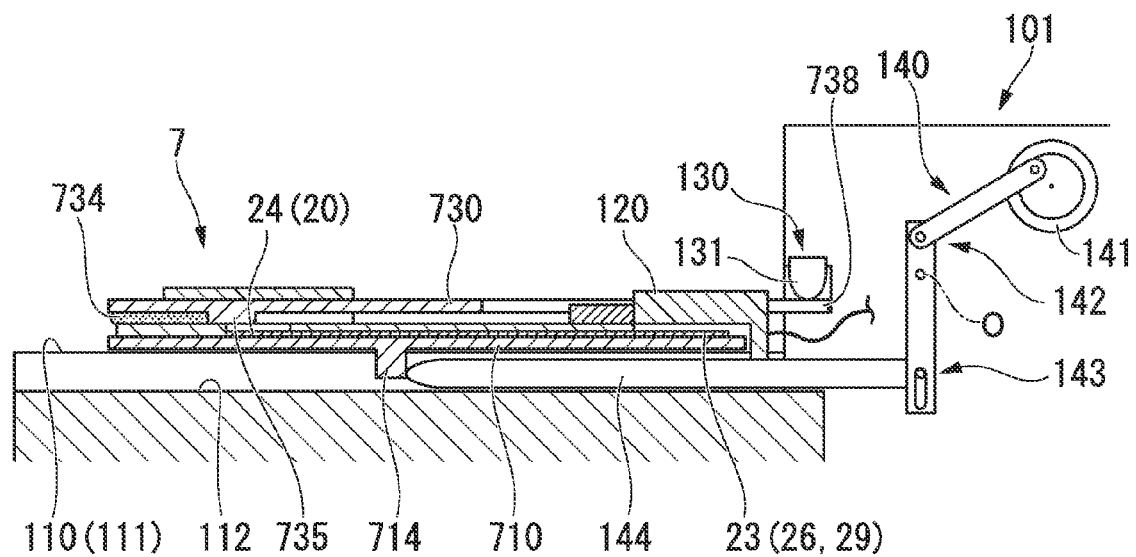
FIG. 11A is an operation explanation diagram illustrating an operation when the detection device is being used.
Figure 11B:
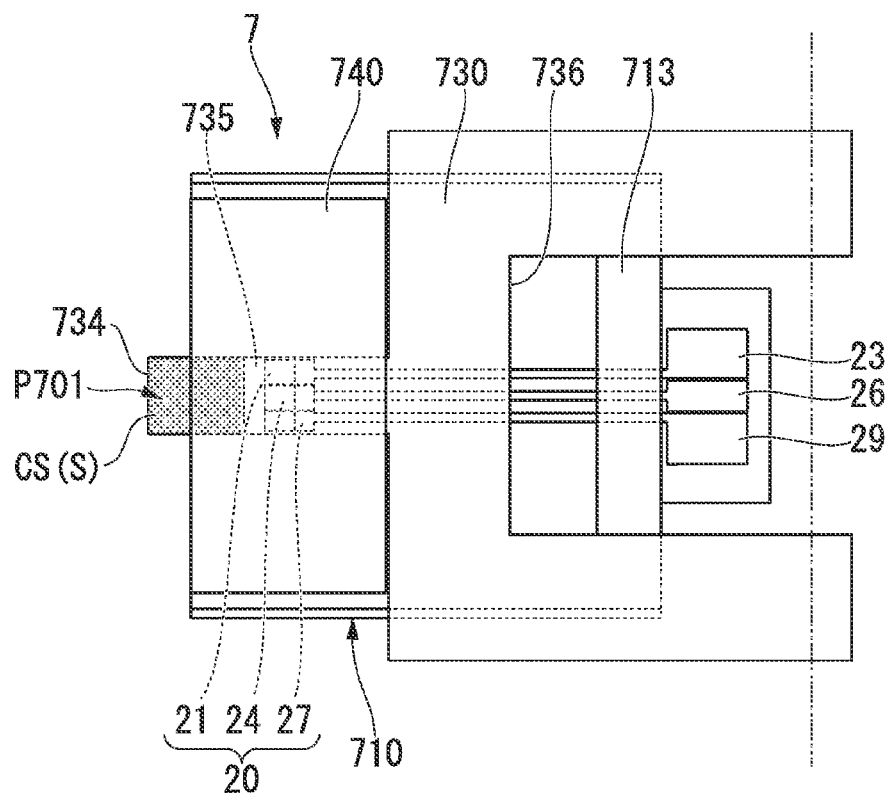
FIG. 11B is an operation explanation diagram illustrating an operation when the detection device is being used.
Figure 12A:
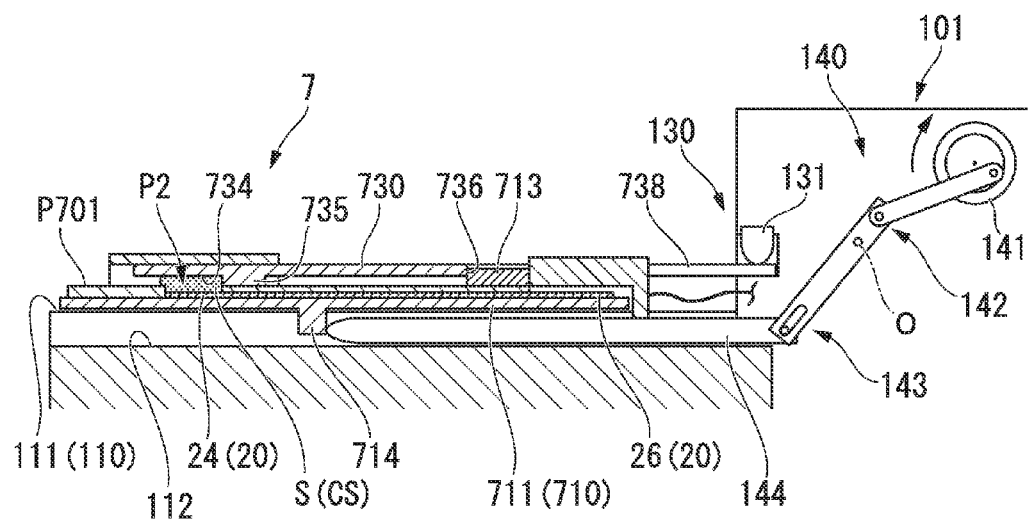
FIG. 12A is an operation explanation diagram illustrating an operation when the detection device is being used.
Figure 12B:
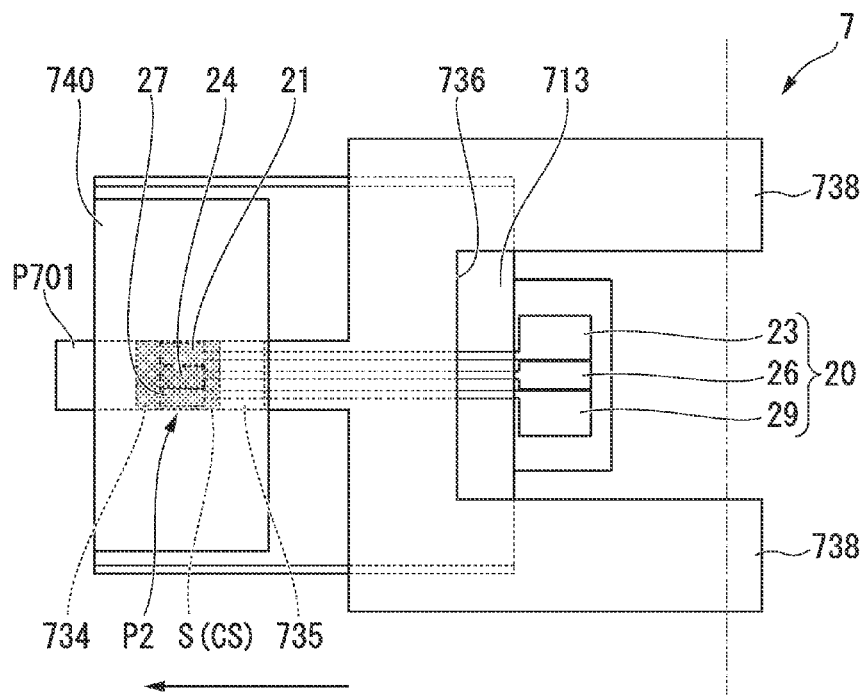
FIG. 12B is an operation explanation diagram illustrating an operation when the detection device is being used.

FIGS. 10A through 10C show the detection device 7. FIG. 10A is a perspective view showing the structure of a portion of the detection device 7, FIG. 10B is a cross-sectional view showing the structure of a portion of the detection device 7, and FIG. 10C is a perspective view showing the structure of a portion of the detection device 7. In addition, FIGS. 11A and 11B are operation explanation diagrams illustrating operations when the detection device 7 is being used. In addition, FIGS. 12A and 12B are operation explanation diagrams illustrating operations when the detection device 7 is being used.

As shown in FIGS. 10A through 10C, the detection device 7 is formed by a base component 710 which is formed from a non-conductive material, a sliding component 730 which performs sliding movements relative to the base component 710 on a surface of the base component 710, and a supporting portion 740 which supports the sliding component 730 such that it is able to slide relative to the base component 710 in the same way as supporting portion 240 of the second embodiment.

The base component 710 has the electrode system 20 described in the first embodiment. The base component 710 can be formed from the same material as that used for the base component 10 described in the first embodiment, and the base component 710 also has the resist layer 12.

A stopper portion 713 that abuts against the sliding component 730 and restricts the amount of sliding movement of the sliding component 730 is provided between the counter electrode 21, working electrode 24, and reference electrode 27 and the contact electrodes 23, 26, and 29 on the surface of the resist layer 12.

Moreover, a sample supply position P701 which is used to supply a sample is set on the opposite side from the contact electrodes 23, 26, and 29 such that the supporting portion 740 is sandwiched in between. In the present embodiment, the sample supply position P701 is provided at a position that protrudes outwards in the surface direction of the base component 710.

Moreover, as shown in FIG. 10B, a projecting portion 714 that protrudes from the surface of the base component 710 is formed on the surface of the base component 710 which is on the opposite side from the side where the electrode system 20 is positioned.

As is shown in FIG. 10C, the sliding component 730 has a sample receptacle portion 734 which is formed in the same way as the sample receptacle portion 234 of the sliding component 230 of the second embodiment, a flow stopping portion 735 which is formed in the same way as the flow stopping portion 235 of the sliding component 230 of the second embodiment, an abutting portion 736 which abuts against the stopper portion 713, and a gripping portion 738 which grips the sliding component 730 when the sliding component 730 is to be made to slide relative to the base component 710.

The preprocessing reagent 13 described in each of the foregoing embodiments can be fixed to the sample receptacle portion 734. Note that the preprocessing reagent 13 may also be placed at the sample supply position P701.

Next, an operation when the detection device 7 of the present embodiment is put to use will be described with reference made to FIG. 11A through FIG. 12B.

Firstly, the schematic structure of an inspection instrument that is used to make an electrochemical measurement of a sample by sliding the sliding component 730 relative to the base component 710 in the detection device 7 of the present embodiment will be described.

As is shown in FIG. 11A, an inspection instrument 101 is provided with a mounting stand 110 on which the base component 710 of the detection device 7 is mounted, a contact portion 120 that makes contact with the contact electrodes 23, 26, and 29 of the base component 710 when this has been mounted on the mounting stand 110, a linking portion 130 that links together with the sliding component 730 when the gripping portion 738 of the sliding component 730 is inserted inside it, and a movement driving section 140 that causes the base component 710 to move backwards or forwards over a mounting surface 111 of the mounting stand 110.

The mounting stand 110 has the mounting surface 111 which is in contact with the base component 710, and a trench portion 112 inside which is inserted the projecting portion 714 of the base component 710. The trench portion 112 is elongated such that a push rod 144 (described below) which it holds is able to move forwards and backwards.

The contact portion 120 is electrically connected to a detection circuit (not shown) that transmits and receives electrical signals via the contact electrodes 23, 26, and 29 of the base component 710.

The linking portion 130 is fixed to the frame of the inspection instrument 101, and has a clamp portion 131 that clamps the gripping portion 738 of the sliding component 730 in the plate-thickness direction thereof.

The movement driving section 140 has a motor 141 which provides rotation drive, a crank portion 142 which is linked to the motor 141 and which converts rotation force from the motor 141 into an oscillating motion centered on a support point O, a link portion 143 that converts the oscillating motion of the crank portion 142 into a forwards-backwards motion in the surface direction of the mounting surface 111, and the push rod 144 which is linked to the link portion 143 and which makes a forwards or backwards movement along the trench portion 112.

A stepping motor or the like whose position is controlled, for example, in synchronization with a pulse signal so as to perform a rotating movement can be employed as the motor 141.

Operations when the detection device 7 of the present embodiment which uses the inspection instrument 101 having the above-described schematic structure is put to use will now be described.

As shown in FIG. 11A, the detection device 7 is prepared when the sliding component 730 has been combined with the base component 710, A user attaches the detection device 7 to the inspection instrument 101 such that the contact electrodes 23, 26, and 29 of the base component 710 are in contact with the contact portion 120, and fixes the gripping portion 738 of the sliding component 730 to the clamp portion 131 of the linking portion 130.

At this time, the projecting portion 714 which is formed on the base component 710 is fitted into the trench portion 112 such that the projecting portion 714 is guided by the trench portion 112. As a result, the base component 710 is able to move relatively to the mounting stand 110 along the direction in which the trench portion 112 extends.

Moreover, as shown in FIG. 11B, the sliding component 730 is inserted into the supporting portion 740, and is positioned such that the sample receptacle portion 734 is located at the sample supply position P701. The sliding component 730 is then attached to the supporting portion 740.

A user supplies the whole blood sample CS to the sample receptacle portion 734 which is located in the sample supply position P701. At this time, because any further flow of the whole blood sample CS which is contained in the sample receptacle portion 734 is blocked by the flow stopping portion 735, the whole blood sample CS does not come into contact with the counter electrode 21, working electrode 24, and reference electrode 27 of the electrode system 20.

A preprocessing reaction is then generated in the whole blood sample CS by the preprocessing reagent 13 which has been fixed to the sample supply position 734, so that the same measurement sample S as in the above-described first embodiment is obtained.

Next, as shown in FIGS. 12A and 12B, the motor 141 provided in the movement driving section 140 of the inspection instrument 101 is rotated. As a result, the push rod 144 performs a rectilinear motion via the crank portion 142 and the link portion 143, and presses the projecting portion 714 of the base component 710 into movement. As a result, the sliding component 730 which is fixed to the inspection instrument 101 moves relatively to the base component 710 which is being pushed by the push rod 144, and the sample receptacle portion 734 which had been positioned at the sample supply position P701 is moved to the overlap position P2 where the counter electrode 21, working electrode 24, and reference electrode 27 of the electrode system 20 are located. When the sample receptacle portion 734 reaches the overlap position P2, the stopper portion 713 which is provided on the base component 710 abuts against the abutting portion 736 of the sliding component 730 so that any further sliding movement thereof is presented.

When the measurement sample S makes contact with each of the counter electrode 21, the working electrode 24, and the reference electrode 27, an electrochemical measurement is performed in a detection circuit (not shown) of the detection instrument 101 by means of the amperometry method (i.e., the current measurement method), the coulometry method (i.e., the electricity quantity measurement method), the phase sweep method, or the cyclic voltammetry method or the like that were described in the first embodiment.

In this type of structure as well, in the same way as in the detection device 1 of the first embodiment, simply by sliding the sliding component 730 relative to the base component 710 after the preprocessing reaction has taken place at the sample supply position P701, the sample is able to reach the overlap position P2 and the reaction required for the electrochemical measurement can be generated. Because of this, multistage processing can be performed safely by means of a simple structure without a complex flow path structure being required.

Furthermore, because the stopper portion 713 is provided in the base component 710, when the sliding component 730 is made to perform a sliding movement relative to the base component 710, the sample receptacle portion 734 can be moved reliably to the overlap position P2.

Fifth Embodiment

Next, a detection device 8 of a fifth embodiment of the present invention will be described with reference made to FIG. 13, and FIGS. 14A and 14B.

Figure 13:
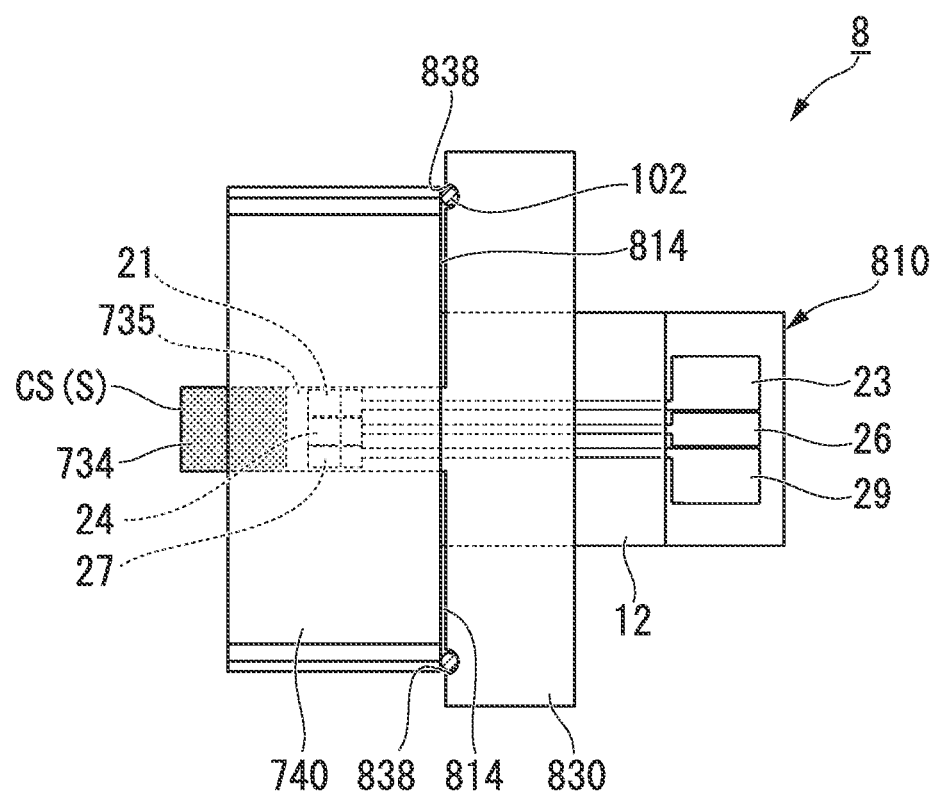
FIG. 13 is a plan view showing a detection device according to a fifth embodiment of the present invention.
Figure 14A:
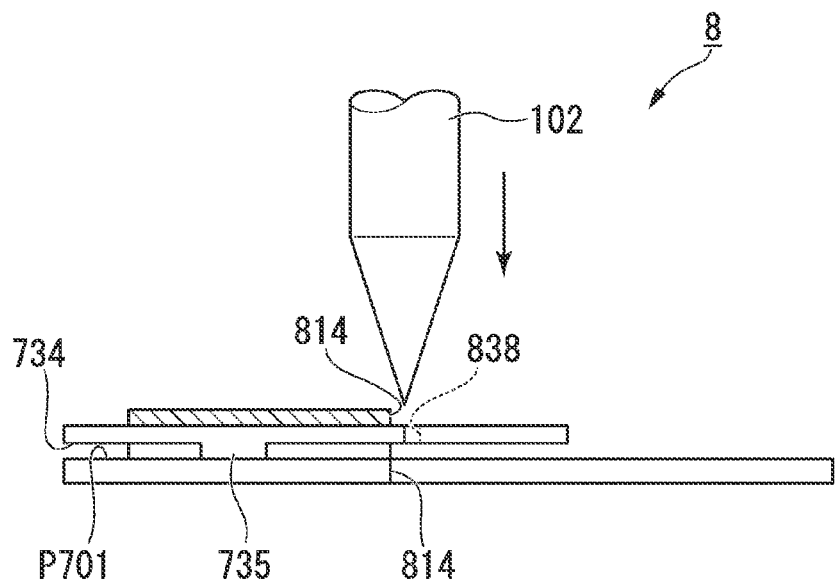
FIG. 14A is an operation explanation diagram illustrating an operation when the detection device is being used.
Figure 14B:
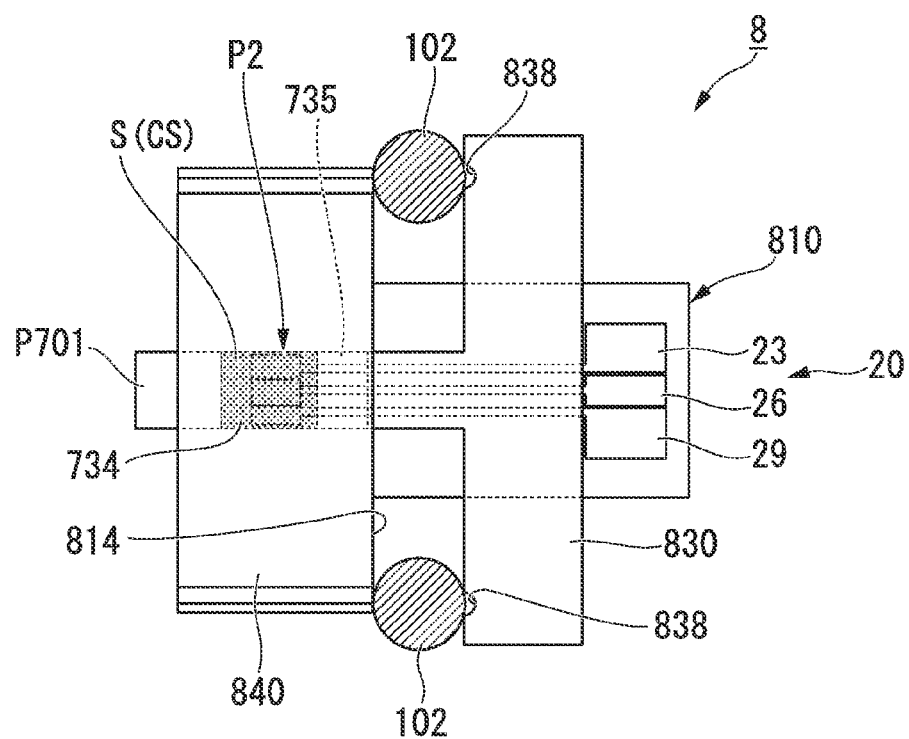
FIG. 14B is an operation explanation diagram illustrating an operation when the detection device is being used.

FIG. 13 is a plan view showing the detection device 8, FIGS. 14A and 14B are operation explanation diagrams illustrating an operation when the detection device 8 is being used.

As shown in FIG. 13, the structure of the detection device 8 differs from that of the detection device 7 of the above-described fourth embodiment in that a base component 810 is provided in place of the base component 710, and a sliding component 830 is provided in place of the sliding component 730.

In the base component 810, no components that correspond to the stopper portion 713 and the projecting portion 714 are provided. Moreover, the base component 810 has the resist layer 12 described in the first embodiment.

Furthermore, the base component 810 also has a wall portion 814 which is positioned between the counter electrode 21, working electrode 24, and reference electrode 27 of the electrode system 20, and the contact electrodes 23, 26, and 29. Note that the wall portion 814 is formed by an outer wall of the supporting portion 740.

In place of the gripping portion 738 which is formed in the above-described sliding component 730, the sliding component 830 has a recessed portion 838 which is formed at a position facing the wall portion 814. The shape of the recessed portion 838 is not particularly limited, however, the recessed portion 838 of the present embodiment is formed having a circular arc-shaped outline.

An operation when the detection device 8 of the present embodiment which has the above-described structure is put to use will now be described with reference made to FIGS. 14A and 14B.

As shown in FIG. 14A, in the present embodiment, an inspection instrument which performs electrochemical measurements using the detection device 8 is provided with a pin 102 that extends in the thickness direction of the base component 810 and the sliding component 830, and whose side which is located closest to the base component 810 and the sliding component 830 is formed having a narrowing diameter.

The pin 102 is attached to the inspection instrument such that it is able to be driven forwards and backwards by a driving mechanism (not shown) which is provided in the inspection instrument.

In the detection device 8, the sliding component 830 is inserted inside the supporting portion 840, and the position of the sample receptacle portion 734 which is formed in the sliding component 830 is matched to the location of the sample supply position P701.

A user attaches the detection device 8 to the inspection instrument. The contact electrodes 23, 26, and 29 of the base component 810 are fixed to the inspection instrument, and are thereby electrically connected to a detection circuit (not shown). Next, the user supplies a whole blood sample CS to the sample receptacle portion 734 of the detection device 8. At this time, the wall portion 814 of the base component 810 abuts against the sliding component 830, and a gap is formed in the recessed portion 838.

Next, the pin 102 is inserted into the gap which is formed by the recessed portion 838 between the wall portion 814 of the base component 810 and the sliding component 830. The pin 102 is then moved in a straight line by the aforementioned driving mechanism provided in the inspection instrument and, as a result of this, the gap between the wall portion 814 and the recessed portion 834 is expanded.

In this manner, as a result of the gap between the wall portion 814 and the recessed portion 838 being expanded, the base component 810 and the sliding component 834 move relatively to each other, and the sample receptacle portion 734 which has been positioned at the sample supply position P701 is moved to the overlap position P2.

In the detection device 8 of the present embodiment as well, in the same way as in the detection device 1 of the above-described first embodiment, simply by sliding the sliding component 830 relative to the base component 810 after the preprocessing reaction has taken place at the sample supply position P701, the sample is able to reach the overlap position P2 and the reaction required for the electrochemical measurement can be generated. Because of this, multistage processing can be performed safely by means of a simple structure without a complex flow path structure being required.

Sixth Embodiment

Next, a detection device 9 of a sixth embodiment of the present invention will be described with reference made to FIG. 15A through FIG. 16B.

Figure 15A:
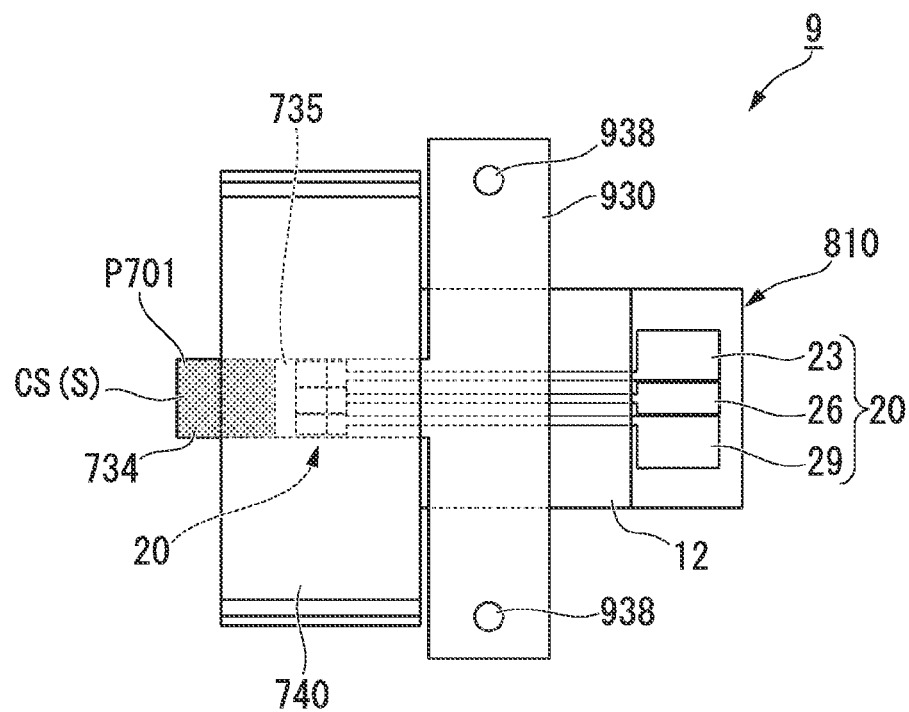
FIG. 15A is a plan view showing a detection device according to a sixth embodiment of the present invention.
Figure 15B:
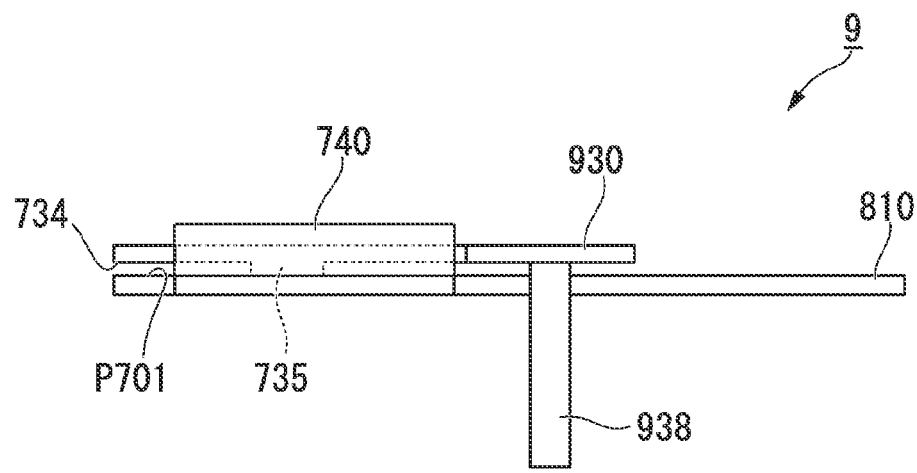
FIG. 15B is a side view of the detection device.
Figure 16A:
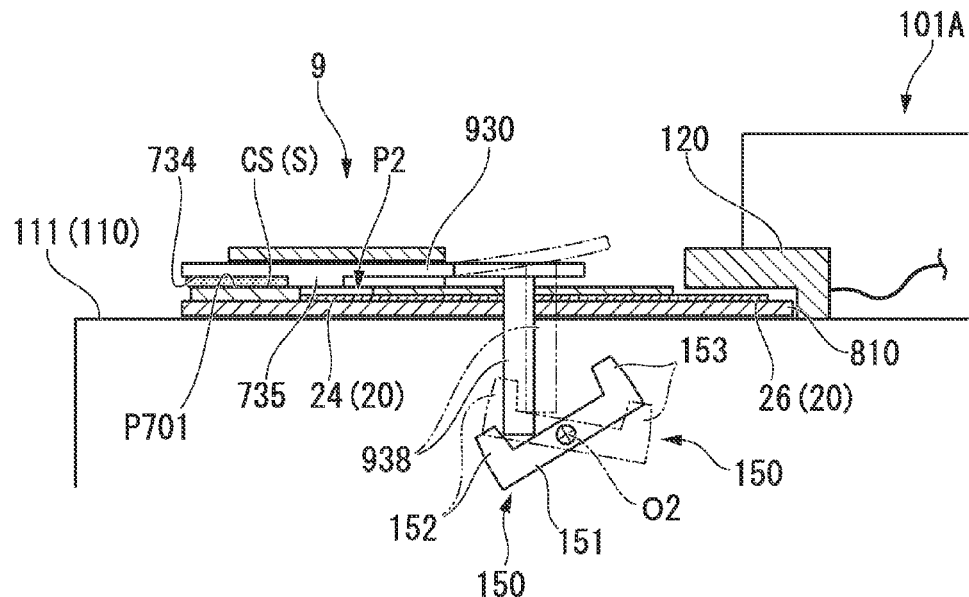
FIG. 16A is an operation explanation diagram illustrating an operation when the detection device is being used.
Figure 16B:
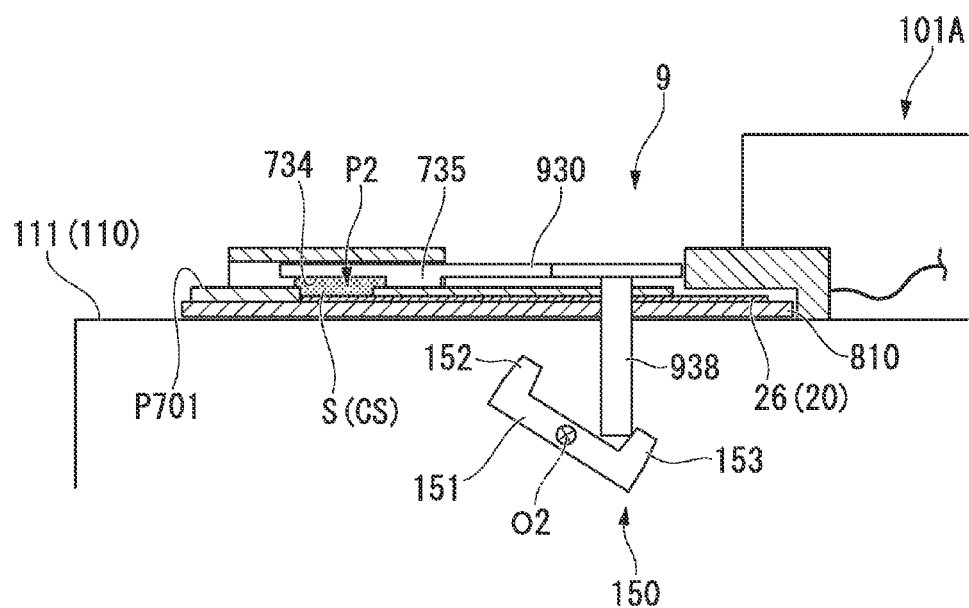
FIG. 16B is an operation explanation diagram illustrating an operation when the detection device is being used.

FIGS. 15A and 15B are respectively a plan view and a side view which show the detection device 9. FIGS. 16A and 16B are operation explanation diagrams illustrating an operation when the detection device 9 is being used.

As shown in FIGS. 15A and 15B, the structure of the detection device 9 differs from that of the detection device 8 of the above-described fifth embodiment in that a sliding component 930 is provided in place of the sliding component 830.

The sliding component 930 does not have the recessed portion 838 of the sliding component 830 which was described in the fifth embodiment, but has a projecting portion 938 which extends in the thickness direction of the sliding component 930.

As shown in FIG. 15B, when the sliding component 930 has been attached to the base component 810, the projecting portion 938 extends onto the opposite side of the base component 810.

Next, the schematic structure of the inspection instrument that is used together with the detection device 9 of the present embodiment will be described with reference made to FIG. 16A.

As shown in FIG. 16A, the structure of an inspection instrument 101A differs from that of the inspection instrument 101 of the above-described fourth embodiment in that it has a movement driving section 150, which is provided in place of the linking portion 130 and the movement driving section 140, and in that the contact portion 120 is fixed to the frame of the inspection instrument 101A.

The movement driving section 150 has a swinging portion 151 which swings around a support point O2. Engaging wall portions 152 and 153 that engage with the projecting portion 938 when the detection device 9 has been set in the inspection instrument 101A are formed on the swinging portion 151.

An operation when the detection device 9 of the present embodiment which utilizes the inspection instrument 101A having the above-described schematic structure is put to use will now be described.

As is shown in FIG. 16A, the detection device 9 is prepared when the sliding component 930 has been combined with the base component 810, and the contact electrodes 23, 26, and 29 of the base component 810 are attached to the contact portion 120. At this time, the projecting portion 938 of the sliding component 930 is engaged with the engaging wall portion 152 of the swinging portion 151.

The sliding component 930 is then inserted in the supporting portion 740, and is placed in position and attached to the supporting portion 740 such that the sample receptacle portion 734 is positioned at the sample supply position P701.

A user supplies the whole blood sample CS to the sample receptacle portion 734 which is located in the sample supply position P701. At this time, because any further flow of the whole blood sample CS which is contained in the sample receptacle portion 734 is blocked by the flow stopping portion 735, the whole blood sample CS does not come into contact with the counter electrode 21, working electrode 24, and reference electrode 27 of the electrode system 20.

A preprocessing reaction is then generated in the whole blood sample CS by the preprocessing reagent 13 which has been fixed in the sample supply position 734, so that the same measurement sample S as in the above-described first embodiment is obtained.

Next, the swinging portion 151 pivots around the support point O2. As a result of this, the projecting portion 938 of the sliding component 930 which is attached to the inspection instrument 101A is pushed upwards. Furthermore, the swinging portion 151 also moves such that the engaging wall portion 153, which is located closer to the contact portion 120, moves away from the sliding component 930. As a consequence, as shown in FIG. 16B, the projecting portion 938 is able to slide over the surface of the swinging portion 151 due to the elasticity of the sliding component 930, and come into contact with the engaging wall portion 153. At this time, the sliding component 930 and the base component 810 move relatively to each other, and the sample receptacle portion 734, which had been positioned at the sample supply position P701, is moved to the overlap position P2 where the counter electrode 21, working electrode 24, and reference electrode 27 of the electrode system 20 are located.

When the measurement sample S comes into contact with each of the counter electrode 21, the working electrode 24, and the reference electrode 27, an electrochemical measurement is performed in the same way as in the first embodiment.

In this type of structure as well, in the same way as in the detection device 1 of the first embodiment, simply by sliding the sliding component 930 relative to the base component 710 after the preprocessing reaction has taken place at the sample supply position P701, the sample is able to reach the overlap position P2 and the reaction required for the electrochemical measurement can be generated. Because of this, multistage processing can be performed safely by means of a simple structure without a complex flow path structure being required.

Note that in the present embodiment, a structure in which the projecting portion 938 is lifted up by the swinging portion 151 is described, however, the present invention is not limited to this, and it is also possible to employ a structure in which the projecting portion 938 is moved in parallel with the surface of the mounting surface 111 of the mounting stand 110 by the engaging wall portion 152 of the swinging portion 151.

As shown in the above-described fourth embodiment, fifth embodiment, and sixth embodiment, it is possible to provide the inspection instrument with a structure that moves the base component of the detection device relatively to the sliding component thereof. At this time, the base component may be fixed to the inspection instrument and the sliding component made to perform a sliding movement relative to the base component, or the sliding component may be fixed to the inspection instrument and the base component made to perform a sliding movement relative to the sliding component. Moreover, because both the timings and the distances of relative movements between the base component and the sliding component can be uniformized, the ease of reproducing measurements made using this detection device can be improved.

Seventh Embodiment

Next, a detection device according to a seventh embodiment of the present invention will be described with reference made to FIG. 17 through FIG. 19. Note that the same symbols are used for component elements that are the same as in the detection devices of each of the above-described embodiments, and any duplicated description thereof is omitted.

Figure 17:
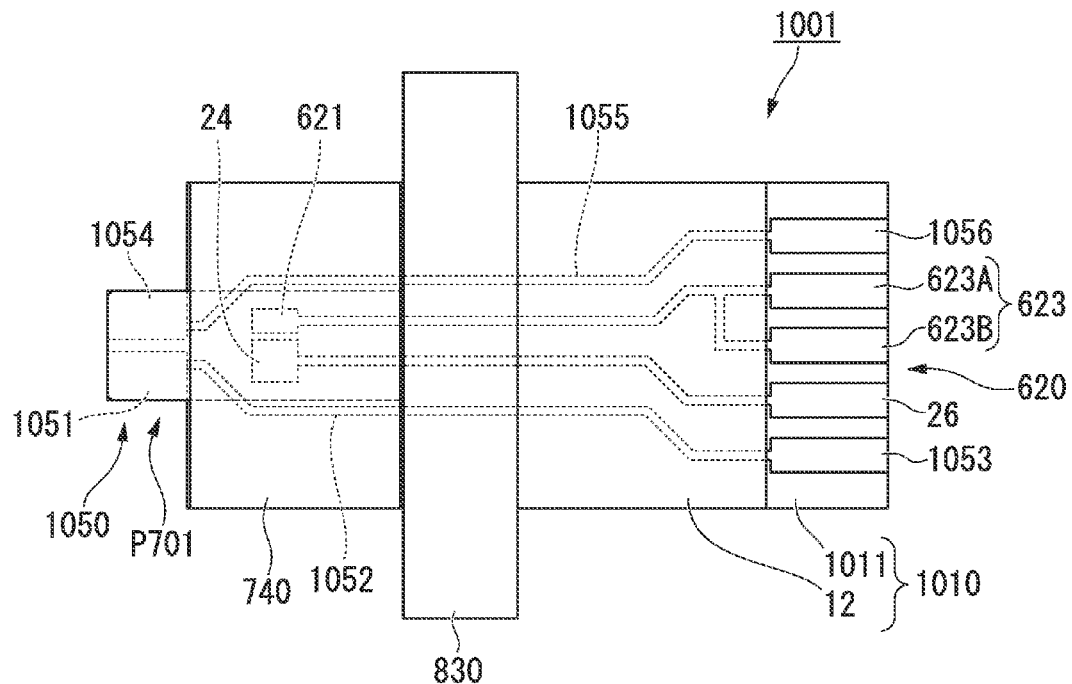
FIG. 17 is a plan view showing a detection device according to a seventh embodiment of the present invention.

FIG. 17 is a plan view showing a detection device 1001 according to the present embodiment. FIG. 18 is a cross-sectional view showing the structure of the detection device 1001. FIG. 19 is an operation explanation diagram illustrating an operation when the detection device 1001 is being used.

Figure 18:
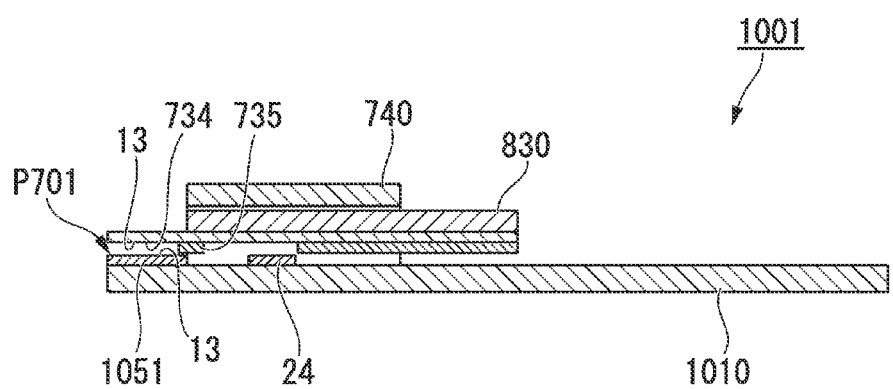
FIG. 18 is a cross-sectional view showing the structure of the device.
Figure 19:
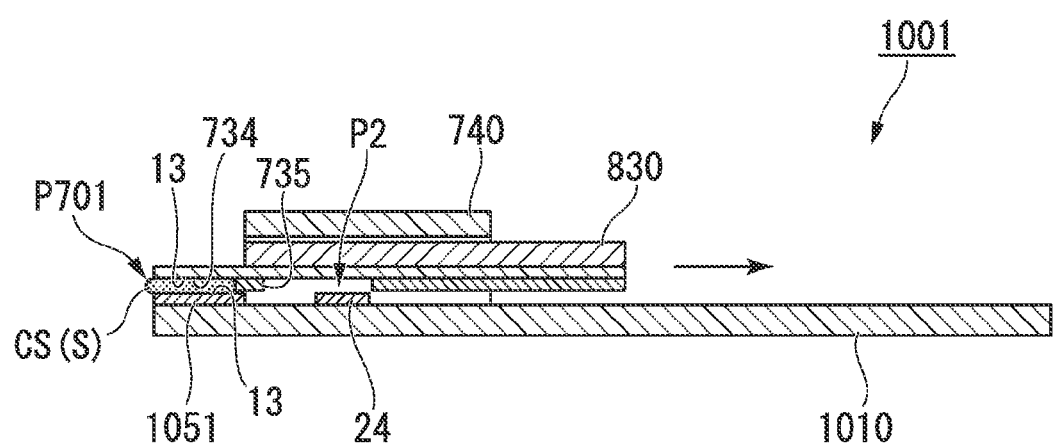
FIG. 19 is an operation explanation diagram illustrating an operation when the detection device is being used.

As is shown in FIG. 17 and FIG. 18, the detection device 1001 of the present embodiment differs from the detection device 8 (see FIG. 13) which was described in the fifth embodiment in that it has a pair of conduction detecting electrodes 1050 at the sample supply position P701, and in that, instead of the electrode system 20 of the fifth embodiment, the electrode system 620 described above in Modified example 3 is provided on a base component 1010, which is provided in place of the base component 810. Moreover, in the present embodiment, it is not necessary to provide the recessed portion 838 in the sliding component 830.

The base component 1010 has a base material 1011 which is formed from the same type of material as the base component 10 and the resist layer 12. In addition, the shape of the base component 1010 differs from that of the above-described base component 810 in that the wall portion 814 is not provided, and is formed in a substantially rectangular plate shape.

The conduction detecting electrode 1050 has a first electrode 1051 and a second electrode 1054 which are placed apart from each other at the sample supply position P701, a wire 1052 and a wire 1055 which are connected respectively to the first electrode 1051 and the second electrode 1054, and a contact electrode 1053 and a contact electrode 1056 which are connected to the wire 1052 and the wire 1055, and which are placed apart from each other so as to sandwich the contact electrode 26 and the contact electrode 623 between them.

The first electrode 1051 and second electrode 1054 of the conduction detecting electrode 1050 are not covered by the resist layer 12, but are instead exposed to the outside. The surfaces of the first electrode 1051 and second electrode 1054 of the conduction detecting electrode 1050 are hydrophilic, and the preprocessing reagent 13 is fixed thereto. In the present embodiment, the preprocessing reagent 13 is fixed to both the conduction detecting electrode 1050 and the sample receptacle portion 734, and when the whole blood sample CS is supplied to the sample supply position P701, the preprocessing reagent 13 can be quickly dissolved in the whole blood sample CS.

Moreover, the wire 1052 and the wire 1055 are covered by the resist layer 12, and are insulated.

In the present embodiment, the contact electrode 623 is formed as separate contact electrodes 623A and 623B in order to make it possible to detect whether or not the detection device 1001 has been correctly inserted into the inspection instrument. As a result of this, the inspection instrument detects that the detection device 1001 has been inserted, and predetermined operations are able to be performed when the detection device 1001 is inserted. Specific examples of predetermined operations that may be performed when the detection device 1001 is inserted include operations such as, for example, automatically turning on the power, turning on the display unit, commencing the conduction detection monitoring, starting the temperature control of the display unit, and the like.

Next, the working of the detection device 1001 of the present embodiment as well as the operations to put this detection device 1001 to use will now be described. The detection device 1001 is used by being attached to an inspection instrument which has a detection circuit that corresponds to each of the contact electrodes 26, 623, 1053, and 1056 and is electrically connected thereto.

When the detection device 1001 is put to use, the detection device 1001 is connected to the above-described inspection instrument. At this time, the sample receptacle portion 734 of the sliding component 830 of the detection device 1001 is placed at the sample supply position P701.

Next, the user pricks a fingertip or the like so that a small droplet of blood appears, and touches the droplet of blood to a portion of the outer edge of the sample supply position P701. As a result, as shown in FIG. 19, at the sample supply position P701 the user's blood is suctioned by capillary phenomenon between the base component 1010 and the sliding component 830, and becomes contained within the sample receptacle portion 734. In the present embodiment, the blood contained between the base component 1010 and the sliding component 830 forms the whole blood sample CS.

The whole blood sample CS which is contained in the sample receptacle portion 734 is blocked by the flow stopping portion 735 so that it does not come into contact with the counter electrode/reference electrode 621 of the electrode system 620 and the working electrode 24. In addition, the preprocessing reagent 13 which is fixed to the first electrode 1051, the second electrode 1054, and the sample receptacle portion 734 is dissolved in the whole blood sample CS which is contained in the sample receptacle portion 734, and a preprocessing reaction begins in the whole blood sample CS.

Furthermore, because the whole blood sample CS comes into contact with both the first electrode 1051 and the second electrode 1054 at the sample supply position P701, the first electrode 1051 and the second electrode 1054 are in a state of conduction. The fact that the first electrode 1051 and a second electrode 1054 are now in a state of conduction can be detected in the inspection instrument to which the detection device 1001 is connected as, for example, a current flowing from the first electrode 1051 to the second electrode 1054.

In the present embodiment, because the first electrode 1051 and the second electrode 1054 become mutually conductive at the timing when the preprocessing reaction begins in the whole blood sample CS, the timing when the preprocessing reaction begins can be detected in the inspection instrument. As a result of this, it is possible to perform processing such as, for example, measuring in the inspection instrument a suitable time for performing the preprocessing reaction, accurately detecting the end of the preprocessing reaction, and notifying the inspection instrument as to the timing when the sliding component 830 should be made to perform a sliding movement. Once the preprocessing reaction has ended, the whole blood sample CS becomes the measurement sample S.

When the preprocessing reaction has ended at the sample supply position P701, the sliding component 830 is gripped by the inspection instrument, and the sliding component 830 is dragged towards the contact electrodes 26 and 623. As a result, the measurement sample S is moved to a position where it is in contact with the counter electrode/reference electrode 621 of the electrode system 620 and the working electrode 24.

Thereafter, electrochemical measurements are made on the measurement sample S in the same way as in each of the above described embodiments.

In the detection device 1001 of the present embodiment, as a result of the pair of conduction detecting electrodes 1050 being provided, the inspection instrument can be made to detect that a sample has been supplied to the sample supply position P701.

Furthermore, because the preprocessing reagent 13 is fixed to the sample supply position P701, the timing when the sample is supplied to the sample supply position P701 can be made to substantially coincide with the timing when the dissolving of the preprocessing reagent 13 in the sample begins. As a consequence, the pair of conduction detecting electrodes 1050 enable the inspection instrument to detect the timing when a preprocessing reaction employing the preprocessing reagent 13 begins.

Note that in the detection device 1001 of the present embodiment, the positions of, for example, the first electrode 1051 and the second electrode 1054 can be placed in suitable locations within the sample supply position P701. By doing this, it is also possible to form a structure in which, for example, when a predetermined quantity or more of the whole blood sample CS has been suctioned inside the sample receptacle portion 734, the first electrode 1051 and the second electrode 1054 are mutually conductive with each other. In this case, the inspection instrument can be made to detect whether or not the required quantity of the whole blood sample CS has been suctioned inside the sample receptacle portion 734.

Eighth Embodiment

Figure 20:
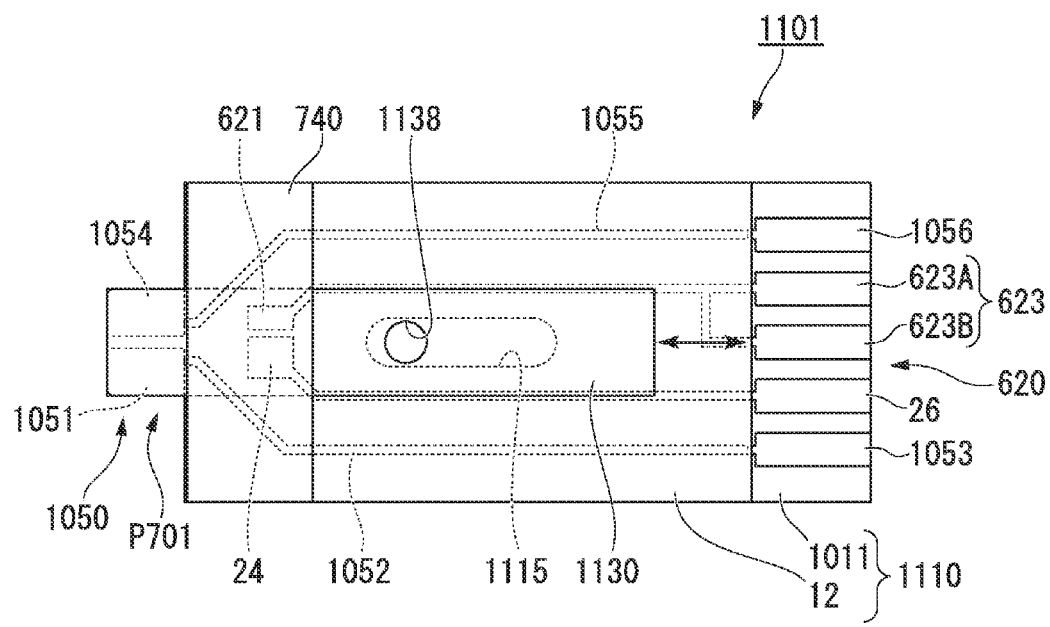
FIG. 20 is a plan view showing a detection device according to an eighth embodiment of the present invention.
Figure 21:
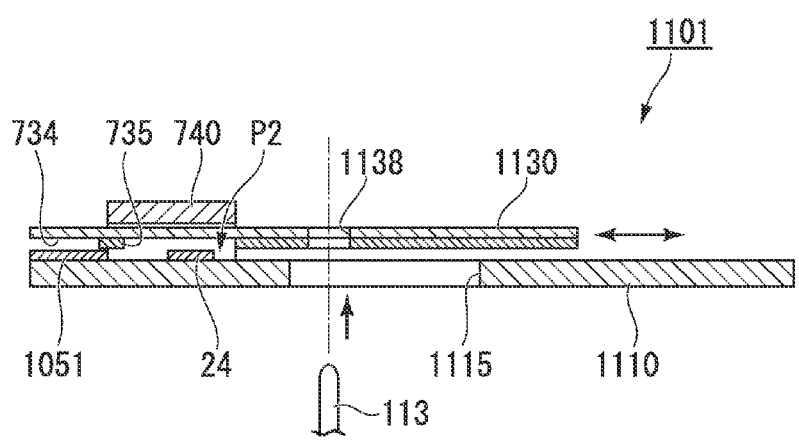
FIG. 21 is an operation explanation diagram illustrating an operation when the detection device is being used.

Next, a detection device of an eighth embodiment of the present invention will be described with reference made to FIG. 20 and FIG. 21. Note that the same symbols are used for component elements that are the same as in the detection devices of each of the above-described embodiments, and any duplicated description thereof is omitted. FIG. 20 is a plan view showing a detection device 1101 of the present embodiment. FIG. 21 is an operation explanation diagram illustrating an operation when the detection device 1101 is being used.

As shown in FIG. 20 and FIG. 21, the structure of the detection device 1101 of the present embodiment differs from that of the detection device 1001 described in the seventh embodiment in that it has a base component 1110 which has substantially the same shape profile as the base component 1010 described in the seventh embodiment and in which an elongated hole 1115 is formed extending in a direction from the sample supply position P701 towards the overlap position P2, and in that a sliding component 1030 is provided place of the sliding component 830.

As shown in FIG. 21, the elongated hole 1115 which is formed in the base component 1110 is formed so as to penetrate the base component 1110 in the thickness direction thereof, and is elongated in the direction in which the sliding component 1030 slides relatively to the base component 1110.

As shown in FIG. 20 and FIG. 21, when seen in plan view, the sliding component 1030 is a rectangular plate-shaped component which is inserted into the supporting portion 740 that is fixed to the surface of the base component 1110. As shown in FIG. 21, a circular through hole 1038 that penetrates the sample receptacle portion 734, the flow stopping portion 735, and the sliding component 1030 in the thickness direction thereof is formed in the sliding component 1030.

When viewed from the thickness direction of the sliding component 1030 with the sliding component 1030 being supported by the supporting portion 740, the through hole 1038 which is formed in the sliding component 1030 is positioned so as to overlap with the elongated hole 1115 which is formed in the base component 1110.

When the detection device 1101 of the present embodiment is being used, using a projection or a rod (indicated by the symbol 113 in FIG. 21) that is able to be inserted through both the elongated hole 1115 and the through hole 1038, the sliding component 1030 can be slid along the elongated hole 1115. As a result, the direction in which the sliding component 1030 is able to make a sliding movement is limited to the direction in which the elongated hole 1115 extends.

In this manner, the elongated hole 1115 which is formed in the base component 1110 functions as a guide when the sliding component 1030 is performing a sliding movement relative to the base component 1110. As a consequence, the sliding component 1030 can be made to perform a precise sliding movement relative to the base component 1110.

Hereinafter, a specific example of the actions when the sliding component places a sample in the sample receptacle portion, and when the sliding component is made to slide over the base component will be described.

Embodiment 1

In the present embodiment, a spacer having a thickness of 0.31 mm is adhered to one side of a plate material manufactured from PET, so that a sample receptacle portion having a gap of 0.31 mm from the base component is formed in the sliding component. The spacer is formed by adhering one surface of two-sided adhesive tape having a thickness of 0.11 mm to a PET film having a thickness of 0.2 mm, and by adhering the other surface of the two-sided adhesive tape to one surface of the PET plate material.

20 µl of a solution obtained by adding a preprocessing reagent to an artificial serum was used as the sample.

Examinations were made of four different conditions that were set for the mutually facing surfaces of the sample receptacle portion and the base component. Namely: when both the sample receptacle portion and the base component were hydrophilic; when the surface of the sample receptacle portion was hydrophobic and the surface of the base component was hydrophilic; when the surface of the sample receptacle portion was hydrophilic and the surface of the base component was hydrophobic; and when both the sample receptacle portion and the base component were hydrophobic.

In the present embodiment, as the method which is used to perform the hydrophilization processing to hydrophilize the sample receptacle portion or the base component, a method is employed in which agarose is coated onto the surface of the resist layer of either the sample receptacle portion or the base component. Moreover, as the method which is used to perform the hydrophobization processing to hydrophobize the sample receptacle portion or the base component, a method is employed in which the PET is exposed without any particular surface processing being specially performed on the base material of the sample receptacle portion or the base component.

As a result, when both the sample receptacle portion and the base component were hydrophilic, the sample was made to flow into the gap between the sample receptacle portion and the base component, and when the sliding component was subsequently made to perform a sliding movement relative to the base component, the sample followed the movement of the sliding component so as to also slide relative to the base component.

Moreover, when the sample receptacle portion was hydrophobic and the base component was hydrophilic, in the same way, the sample was made to flow into the gap between the sample receptacle portion and the base component, and when the sliding component was subsequently made to perform a sliding movement relative to the base component, the sample followed the movement of the sliding component so as to also slide relative to the base component.

Moreover, when the sample receptacle portion was hydrophilic and the base component was hydrophobic, in the same way, the sample was made to flow into the gap between the sample receptacle portion and the base component, and when the sliding component was subsequently made to perform a sliding movement relative to the base component, the sample followed the movement of the sliding component so as to also slide relative to the base component.

Moreover, when both the sample receptacle portion and the base component were hydrophobic, although it was possible for the sample to be contained between the sample receptacle portion and the base component, there were cases when the sample was repelled when an attempt was made to allow it to flow between the sample receptacle portion and the base component. Moreover, when a sample was being contained in the sample receptacle portion, when the sliding component was made to perform a sliding movement relative to the base component, the sample followed the movement of the sliding component so as to also slide relative to the base component.

From the results obtained from the above Embodiment 1, it was found that it is preferable for at least one of the mutually facing surfaces of the sample receptacle portion and the base component to be hydrophilic in order for a sample to be able to flow into the sample receptacle portion and perform a sliding movement over the base component.

Embodiment 2

Next, Embodiment 2 in which the composition of the sample used in Embodiment 1 was changed is shown.

In the present embodiment, 20 µl of a solution obtained by adding a preprocessing reagent to human whole blood was used as the sample. In the present embodiment, the behavior which was exhibited when the sample was made to flow into the sample receptacle portion, and the sample was then made to slide over the base component was the same as that observed in Embodiment 1.

Embodiment 3

Next, Embodiment 3 in which the thickness of the spacer in the sample receptacle portion which was used in the Embodiment 1 was changed is shown.

In the present embodiment, a structure was employed in which the thickness of the spacer was set at four times the thickness of the spacer used in Embodiment 1, namely, was set to a thickness of 1.24 mm. This spacer was formed by adhering one surface of two-sided adhesive tape having a thickness of 0.11 mm to a PET film having a thickness of 0.2 mm, and then superimposing four of these on top of each other and adhering the resulting object to one surface of a PET plate material.

Moreover, 20 μl of a solution obtained by adding a preprocessing reagent to an artificial serum, in the same way as in Embodiment 1, was used as the sample.

In the present embodiment, although the same type of results were obtained as those obtained from Embodiment 1, when the sample did not adhere to the sample receptacle portion, then even when the sliding component was made to slide over the base component, the sample did not slide over the base component. From these results it was found that it is preferable for the thickness of the spacer to be such that, after considering the quantity of sample to be used in the measurement, the sample is able to adhere to the sample receptacle portion.

Embodiment 4

Next, Embodiment 4 in which the composition of the sample used in Embodiment 3 was changed is shown.

In the present embodiment, 20 μl of a solution obtained by adding a preprocessing reagent to human whole blood was used as the sample. In the present embodiment, the behavior which was exhibited when the sample was made to flow into the sample receptacle portion, and the sample was then made to slide over the base component was the same as that observed in Embodiment 3.

Embodiment 5

Next, an embodiment in which human whole blood was measured using the detection device 2 of the second embodiment of the present invention is shown.

In the present embodiment, preprocessing reagents having the compositions shown in Table 1 were fixed to the sample receptacle portion 234 of the sliding component 230. The pH of the preprocessing reagents was set to 7.7. The preprocessing reagents were fixed to the sample receptacle portion 234 by means of a method in which 6 μl of the preprocessing reagents were coated onto the wall surfaces of the sample receptacle portion 234, and these were then dried at 50° C. for 30 minutes.

TABLE 1

| Reagent | Final concentration |
|---|---|
| 2-[4-(2-hydroxyethyl)-1-piperazine] ethane sulfonic acid | 10.0 mM |
| Phosphoenolpyruvic acid monosodium salt | 147.0 mM |
| Adenosine-5'-3 phosphoric acid | 10.4 mM |

TABLE 1-continued

| Reagent | Final concentration |
|---|---|
| Pyruvic acid kinase | 120.0 U/mL |
| Glucokinase | 30.0 U/mL |
| Ascorbic acid oxidase | 20.0 U/mL |
| Magnesium chloride | 17.6 mM |
| Potassium chloride | 17.6 mM |
| Sodium azide | 0.1% |
| Ethylene-diamine-tetraacetic acid disodium salt | 0.1 mM |

Moreover, measuring reagents having the compositions shown in Table 2 were fixed to the electrode system 20 of the base component 10. The measuring reagents were fixed to the electrode system 20 by means of a method in which 2 μl of the measuring reagents were coated on the electrode system 20, and they were then dried at 50° C. for 5 minutes.

TABLE 2

| Reagent name | Concentration |
|---|---|
| Thionine acetate | 120 μmol/L |
| 1,5-AG dehydrogenase | 3 U/mL |
| o-sulfobenzoic acid cyclic | 50 mM |
| Nafion | 0.1% |

Moreover, as the human whole blood samples used in the present embodiment, four examples (Specimens A, B, C, and D) of venous blood of a normal healthy person which were collected in blood-collecting vessels in which EDTA-2K (dipotassium ethylenediaminetetraacetic acid) had been previously enclosed were used.

The procedure for measuring the above-described human whole blood samples in the present embodiment is described below.

Firstly, the sliding component 230 was set on the base component 10 such that the sample receptacle portion 234 was located at the sample supply position P201. Next, using a micropipette, 6 μl of the human whole blood sample CS were supplied to the sample receptacle portion 234. The human whole blood sample CS was then left standing for five minutes at the sample supply position P201, and a preprocessing reaction created by the preprocessing reagent fixed to the sample receptacle portion 234 was allowed to proceed for five minutes.

After five minutes had elapsed after the human whole blood sample CS had been supplied to the sample receptacle portion 234 which was located at the sample supply position P201, the sliding component 230 was made to slide relative to the base component 10 such that the sample receptacle portion 234 was moved from the sample supply position P201 to the overlap position P2. The human whole blood sample CS was changed by the preprocessing reaction to the measurement sample S, and the measurement sample S was then moved from the sample supply position P201 to the electrode system 20 by causing the sliding component 230 to slide relative to the base component 10.

After the measurement sample S had been placed in contact with the electrode system 20 of the detecting section, electrochemical measurements were made using an amperometry method. In the amperometry method, 0V of electric potential were applied to the reference electrode 27, and the electric current value was detected after 5 seconds had elapsed from the commencement of this application. This current value was then applied to a predetermined calibration formula, and the 1,5-AG concentration in the measurement sample S was calculated.

The above-described operation was then repeated for each of the human whole blood samples of the four examples, and electrochemical measurements of each sample were taken.

Moreover, as a control experiment, the 1,5-AG concentration was measured using an existing method.

The procedure for the control experiment was as follows. Firstly, blood plasma was separated using centrifugal force from the above-described four samples of human whole blood. Using a Lana 1,5-AG Auto Liquid (manufactured by Nippon Kayaku Co., Ltd.) and a Hitachi 7150 Chemistry Analyzer, the concentrations of 1,5-AG in the blood serums were measured using the detection methods described in the attached documentation of these instruments.

The results from the electrochemical measurements of the present embodiments and the results from the measurements taken from the control experiments (i.e., comparative examples) are shown in Table 3.

TABLE 3

| Specimen | Comparative example (µg/mL) | Example (µg/mL) |
|---|---|---|
| A | 36.9 | 37.4 |
| B | 14.0 | 14.8 |
| C | 19.5 | 19.7 |
| D | 24.9 | 25.2 |

As is shown in Table 3, the electrochemical measurements that were made using the detection device 2 of the present embodiments have a high correlation with the measurements made using the existing method, and by using the detection device 2 in the present embodiments, it was found that it is possible to measure the 1,5-AG concentration of a human whole blood sample with the same high level of accuracy as when the existing method is used.

Embodiments of the present invention have been described above with reference made to the attached drawings, however, the specific structure of the present invention is not limited to these embodiments, and various design modifications and the like may be made insofar as they do not depart from the spirit or scope of the present invention.

For example, in each of the above-described embodiments, an example is given in which preprocessing is achieved via a preprocessing reagent that is fixed to the sample supply position, however, the present invention is not limited to this, and procedures such as, without using a preprocessing reagent or the like, leaving the sample standing at the sample supply position for a stipulated time period, heating or cooling the sample at the sample supply position, and irradiating electromagnetic waves or light onto the sample at the sample supply position may also correspond to the preprocessing of the present invention.

Moreover, as the material used to form the electrode system 20, in addition to conductive carbon, it is also possible to use gold, platinum, palladium or silver, silver/silver chloride, nickel, copper, titanium, iridium, lead, tin oxide, platinum black and the like.

Instead of forming the electrode system 20 by employing a screen printing method, it is also possible to employ various types of vapor deposition methods such as a vacuum deposition method or an electroless plating method, or to employ a sputtering method, a foil adhesion method, or a plating method or the like.

Moreover, instead of forming the electrode system 20 directly on top of the substrate 11, it is also possible to construct an electrode system by coating a metallic thin film or the like onto a separate substrate so as to create an electrode component, and then fixing this onto the substrate 11 by means of an adhesive or the like.

Moreover, an example has been described above in which the through hole 33 is formed in the slide body 32, however, the present invention is not limited to this and it is also possible to form a recessed portion in place of a through hole in the surface of the slide body 32 that faces the base component 10.

Moreover, in the above-described embodiment, an example is described in which the preprocessing reagent 13 is fixed to the sample receptacle portion 34, 234, however, the present invention is not limited to this and it is also possible for the preprocessing reagent to be fixed onto the resist layer 12 at the sample supply position P1, P201.

The method used to position the preprocessing reagent 13 may also be one in which the preprocessing reagent 13 is fixed to the sample supply position P1, P201 or the sample receptacle portion 34, 234 by means of a method such as dipping or spin-coating or the like. Alternatively, the preprocessing reagent 13 may be fixed to the sample supply position P1, P201 or the sample receptacle portion 34, 234 by means of a method in which filter paper which has been impregnated with the preprocessing reagent 13 and then dried is adhered thereto, or a method in which an active group is introduced to a carrier such as microbeads or the like and these microbeads are then placed on the sample supply position P1, P201 or in the sample receptacle portion 34, 234.

Moreover, in the above-described embodiments, examples are described in which the task of making the respective sliding components 30 and 230 perform a sliding movement relative to the base component 10 is a manual task performed by a user, however, the present invention is not limited to this and it is also possible provide, either integrally with or independently from the above-described inspection instrument, a moving mechanism that grips the sliding component 30 or 230 and the base component 10, and causes the sliding component 30 or 230 to slide relative to the base component 10. In this case, it is possible for the operation to slide the sliding component to be automated. In the above-described fourth through sixth embodiments, an example of a structure for automating the operation to slide the sliding component is given. Note that the structure of the moving mechanism that causes the sliding component to slide is not limited to these structures. For example, as the structure that causes the base component and the sliding component to move relatively to each other, it is also possible to employ a rack-and-pinion-based structure, or a worm-gear and worm-wheel-based structure, or the like.

Moreover, examples of a typical oxidation-reduction enzyme that may be used include glucose oxidase and glucose dehydrogenase, lactate oxidase, cholesterol oxidase and cholesterol dehydrogenase, galactose oxidase, uricase, ascorbate oxidase, pyruvate oxidase, and lactate dehydrogenase and the like.

As the preprocessing reagent, it is also possible for another suitable reagent to be employed provided that it includes a reagent that removes or captures ascorbic acid, or uric acid or the like, or that converts these into another substance that has no effect on the detection.

Note that, in addition to reagents that elicit an enzymatic reaction or a chemical reaction, the preprocessing reagent may also be one that performs ion absorption or affinity absorption, or absorbs and captures specific substances as a boric acid complex, or may be one that is able to complementarily capture specific substances such as hormones and receptors, antigens and antibodies, and RNA and DNA and the like. Furthermore, these preprocessing reagents may also be formed by solidifying the reagent on a carrier such as microbeads or microspheres.

Moreover, the surfaces of the guide portions described in each of the above-described embodiments may also be hydrophobic. In this case, it is possible to obstruct the sample from entering between the supporting portion and the sliding component. In particular, as is described above in the second embodiment and the fourth through eighth embodiments, when a structure is employed in which a sample which is contained in the sample receptacle portion comes into contact with the supporting portion, by making the surface of the guide portion hydrophobic, the quantity of sample that is used for the preprocessing reaction and for the subsequent detection can be accurately maintained.

Moreover, the component elements illustrated in the above-described embodiments and modified examples thereof may also be combined into suitable structures,

INDUSTRIAL APPLICABILITY

The detection device of the present invention can be used together with an apparatus that makes a medical examination by analyzing a biological sample. In particular, the detection device of the present invention is excellent for use as a detection device that makes an examination that requires a multistage reaction in a liquid biological sample such as blood and the like.

DESCRIPTION OF THE REFERENCE NUMERALS 1, 2, 3, 4, 5, 6, 7, 8, 9, 1001, 1101 . . . Detection devices
10, 310, 710, 810, 1010, 1110 . . . Base components
20, 620 . . . Electrode systems (Detecting sections)
21 . . . Counter electrode
24 . . . Working electrode
27 . . . Reference electrode
30, 230, 330, 430, 530, 730, 830, 930, 1030 . . . Sliding components
32, 232 . . . Slide bodies
32a, 32b . . . Notches (Flow restricting portions)
33 . . . Through hole (Flow stopping portion)
34, 234, 734 . . . Sample receptacle portions
40, 240, 440, 540, 740 . . . Supporting portions
41, 241, 444 . . . Guide portions
42 . . . Covering component (Covering portion)
235, 333, 735 . . . Flow stopping portions
320, 320a . . . Optical measuring sections (Detecting sections)
1050 . . . Conduction detecting electrode
1115 . . . Elongated hole
1038 . . . Through hole
P1, P201, P701 . . . Sample supply positions
P2 . . . Overlap position
CS . . . Whole blood sample (Sample)
S . . . Measurement sample

What is claimed is:

1. A detection device that is used to detect a sample, comprising:
   a base component that is non-conductive and has on its surface a sample supply position to which the sample is supplied;
   a detecting section that is formed at a distance from the sample supply position on the surface of the base component, and has an electrode system that includes a working electrode, a reference electrode, and a counter electrode that are formed on the surface of the base component at a distance from the sample supply position;
   a sliding component having a slide body that performs a sliding movement over the surface of the base component, and also having a sample receptacle portion that is provided in a portion of the slide body and is capable of containing the sample, said sliding component also having a flow stopping portion positioned between an overlap position and a sample supply position when the sample receptacle portion is located at the sample supply position, said flow stopping portion stopping the flow of the sample from the sample receptacle portion to the electrode system formed in a portion of the slide body; and
   a supporting portion that is fixed to the base component and supports the sliding component such that it is capable of performing the sliding movement relative to the base component, wherein the base component and the sliding component are able to perform the sliding movement within a range that includes the overlap position, where the sample receptacle portion overlaps with the detecting section, and the sample supply position, wherein
   the flow stopping portion is formed on the sliding component so as to protrude from the sliding component in the direction of the base component when the sliding component is mounted on the base component.

2. A detection device that is used to detect a sample, comprising:
   a base component that is non-conductive and has on its surface a sample supply position to which the sample is supplied;
   a detecting section that is formed at a distance from the sample supply position on the surface of the base component, and has an electrode system that includes a working electrode, a reference electrode, and a counter electrode that are formed on the surface of the base component at a distance from the sample supply position;
   a sliding component having a slide body that performs a sliding movement over the surface of the base component, and also having a sample receptacle portion that is provided in a portion of the slide body and is capable of containing the sample, said sliding component also having a flow stopping portion positioned between an overlap position and a sample supply position when the sample receptacle portion is located at the sample supply position, said flow stopping portion stopping the flow of the sample from the sample receptacle portion to the electrode system formed in a portion of the slide body; and
   a supporting portion that is fixed to the base component and supports the sliding component such that it is capable of performing the sliding movement relative to the base component,
   wherein the base component and the sliding component are able to perform the sliding movement within a range that includes the overlap position, where the sample receptacle portion overlaps with the detecting section, and the sample supply position, and
   wherein the flow stopping portion has a hole portion or a recessed portion in which, when viewed from a top direction of the detection device, at least a part of an edge portion thereof is positioned between the overlap position and the sample supply position when the sample receptacle portion is located at the sample supply position.

3. The detection device according to claim 2, wherein the detecting section is formed so as to be capable of making electrochemical measurements.

4. The detection device according to claim 2, wherein at least one of the mutually facing portions of the sample receptacle portion and the base component is formed such that at least a portion thereof is hydrophilic.

5. The detection device according to claim 2, wherein supporting portions are provided in two locations that are separated from each other such that the overlap position is sandwiched between them on the base component.

6. The detection device according to claim 2, wherein the supporting portion has guide portions, and these guide portions are separated from each other such that the overlap position is sandwiched between them on the base component, and the guide portions are also provided in parallel with each other.

7. The detection device according to claim 2, wherein the supporting portion has a covering portion that covers the overlap position such that a gap through which the sliding component is capable of moving backwards and forwards is created between the covering portion and the base component.

8. The detection device according to claim 2, wherein the sliding component has flow restricting portions between the slide body and the sample receptacle portion that restrict the flow of the sample from the sample receptacle portion towards the slide body.

9. The detection device according to claim 8, wherein the flow restricting portion is formed by cutting notches in a portion of the slide body adjacent to the sample receptacle portion.

10. The detection device according to claim 2, wherein a preprocessing reagent that is used in preprocessing in order to either remove or capture any interfering substances that may obstruct the detection, or to convert such interfering substances into another substance that has no effect on the detection is placed on at least one of the sample receptacle portion and the sample supply position.

11. The detection device according to claim 3, wherein at least one of the counter electrode and the reference electrode is a silver-silver chloride electrode which employs silver and silver chloride.

12. The detection device according to claim 2, further comprising:
a pair of conduction detecting electrodes that are located apart from each other and are exposed on the surface of the base component at the sample supply position, wherein the pair of conduction detecting electrodes are made conductive with each other by the sample that is supplied to the sample supply position.

13. The detection device according to claim 12, wherein a surface of the conduction detecting electrodes is hydrophilic.

14. The detection device according to claim 6, wherein the guide portions are hydrophobic.

15. The detection device according to claim, 2, wherein
an elongated hole that is elongated in a sliding direction in which the sliding component slides relative to the base component is formed in the base component; and
a through hole that, when viewed from the thickness direction of the sliding component, overlaps with the elongated hole when the sliding component is being supported by the supporting portion is formed in the sliding component.

16. The detection device according to claim 3, wherein an oxidation-reduction enzyme and a redox mediator are placed on at least the working electrode of the electrode system.

17. The detection device according to claim 16, wherein the redox mediator includes at least one selected from ruthenium derivatives, osmium derivatives, ferricyan derivatives, ferrocene derivatives, quinine derivatives, phenothiazine derivatives, phenoxazine derivatives, phenazine derivatives, indophenol derivatives, diphenylamine derivatives, and phenol derivatives.

18. The detection device according to claim 16, wherein the oxidation-reduction enzyme includes at least one selected from pyranose oxidase, L-sorbose oxidase, 1,5-AG dehydrogenase, L-sorbose dehydrogenase, and 1,5-anhydroglucitol-6-phosphate dehydrogenase.

19. The detection device for performing 1,5 anhydroglucitol according to claim 10, wherein the preprocessing reagent contains a reagent that either removes or captures glucose, or else converts glucose into another substance that has no effect on the detection.

* * * * *